(12) United States Patent
Pert et al.

(10) Patent No.: US 10,130,674 B2
(45) Date of Patent: Nov. 20, 2018

(54) MODIFIED PEPTIDE THAT REDUCES PAIN IN PERIPHERAL NEUROPATHY

(75) Inventors: Candace Pert, Potomac, MD (US); Michael Ruff, Potomac, MD (US)

(73) Assignee: Creative Bio-Peptides, Potomac, MD (US)

( * ) Notice: Subject to any disclaimer, the term of this patent is extended or adjusted under 35 U.S.C. 154(b) by 0 days.

(21) Appl. No.: 13/024,324

(22) Filed: Feb. 10, 2011

(65) Prior Publication Data

US 2011/0245180 A1 Oct. 6, 2011

Related U.S. Application Data

(60) Provisional application No. 61/302,933, filed on Feb. 9, 2010.

(51) Int. Cl.

| A61K 31/08 | (2006.01) |
|---|---|
| A61K 38/00 | (2006.01) |
| A61K 38/08 | (2006.01) |
| C07K 14/005 | (2006.01) |

(52) U.S. Cl.
CPC ............ *A61K 38/08* (2013.01); *C07K 14/005* (2013.01); *C12N 2740/16122* (2013.01)

(58) Field of Classification Search
None
See application file for complete search history.

(56) References Cited

U.S. PATENT DOCUMENTS 6,265,374 B1 * 7/2001 Andersen et al. ............ 514/1.3

* cited by examiner

*Primary Examiner* — Christine J Saoud
*Assistant Examiner* — Jon M Lockard
(74) *Attorney, Agent, or Firm* — Scott Houtteman; Kile Park & Houtteman PLLC

(57) ABSTRACT

Chemokine signaling is important in neuropathic pain, with microglial cells expressing CCR2 playing a well established key role. DAPTA, a gp120-derived CCR5 entry-inhibitor has been shown to inhibit CCR5-mediated monocyte migration and to attenuate neuroinflammation. We disclose here that as a stabilized analog of DAPTA, the short peptide All D TTNYT (SEQ ID NO:1) exhibits potent antagonism for both CCR2 ($IC_{50}$ 4.2 pM) and CCR5 ($IC_{50}$ 0.18 pM) in monocyte chemotaxis. Oral administration of All D TTNYT (SEQ ID NO:1) (0.05-1 mg/kg) for 7 days fully prevents mechanical allodynia and inhibits the development of thermal hyperalgesia following partial ligation of the sciatic nerve in rats. Administered from day 8 to day 12, All D TTNYT (SEQ ID NO:1) (0.2-1 mg/kg) reverses already established hypersensitivity. All D TTNYT (SEQ ID NO:1) relieves pain hypersensitivity probably through either or both CCR2 and CCR5, since by using genetically deficient animals, we demonstrated that in addition to CCR2, CCR5 is also required for the development of neuropathic pain. Moreover, All D TTNYT (SEQ ID NO:1) is able to reduce spinal microglial activation, monocyte infiltration, and to inhibit inflammatory responses evoked by peripheral nerve injury that cause chronic pain. Our findings suggests that the targeting CCR2/CCR5 should provide greater efficacy than targeting CCR2 or CCR5 alone and dual CCR2/CCR5 antagonist All D TTNYT (SEQ ID NO:1) has the potential for broad clinical use in neuropathic pain treatment.

4 Claims, 12 Drawing Sheets

Specification includes a Sequence Listing.

Figures 2A-B
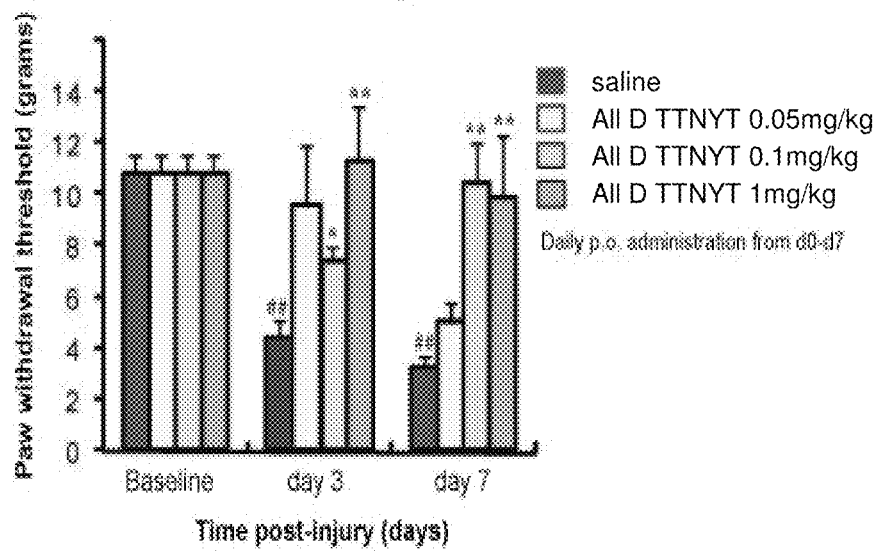
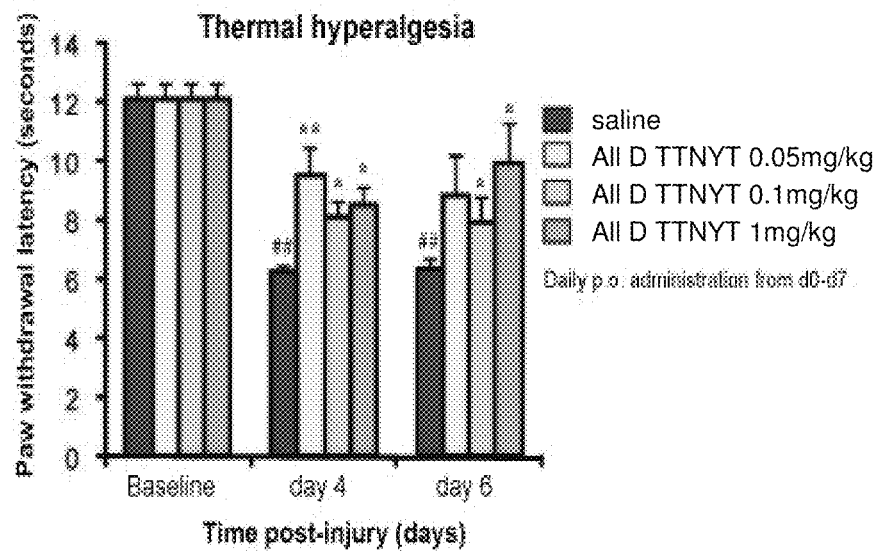

Figures 3A-B
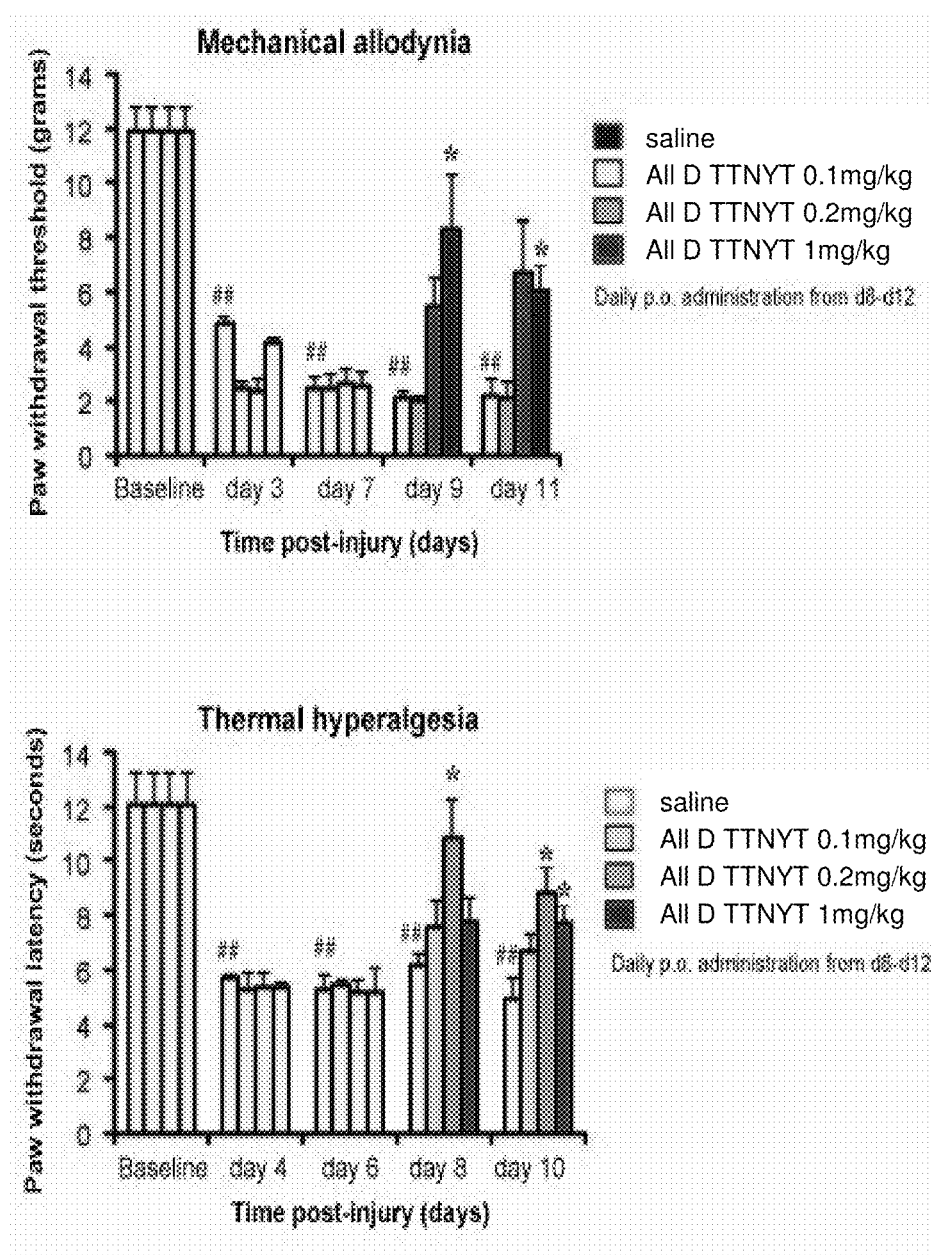

Figures 4A-D
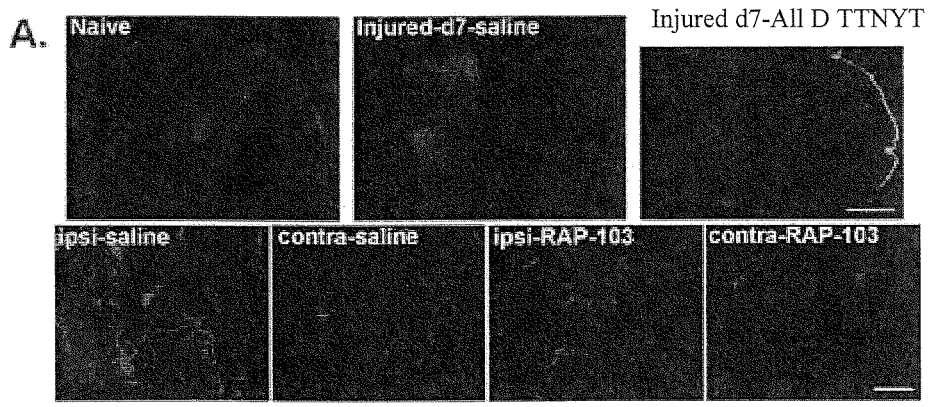
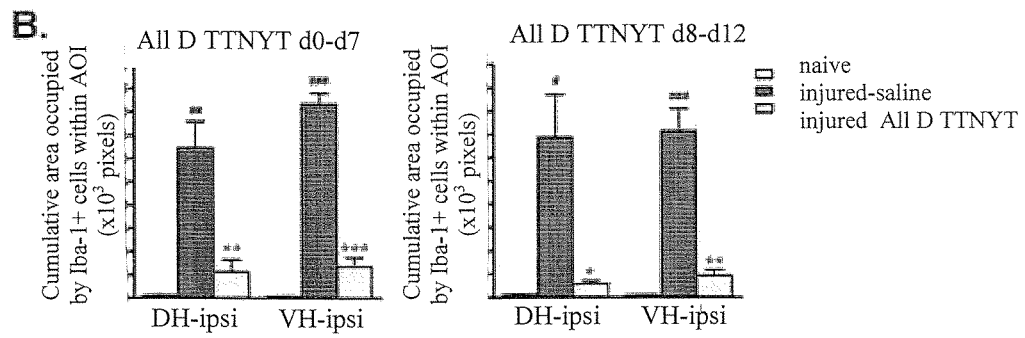
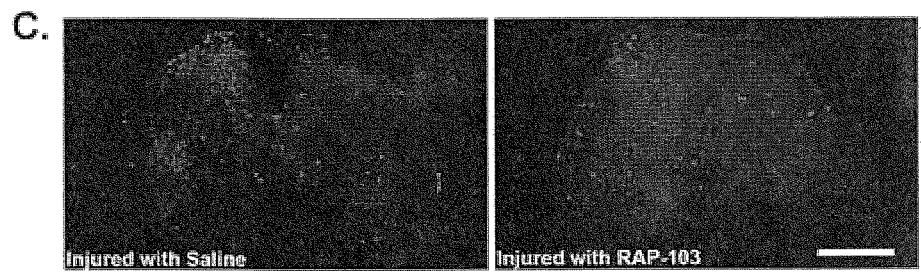
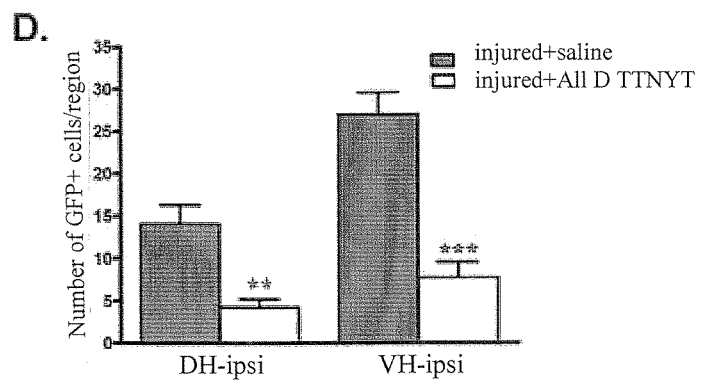

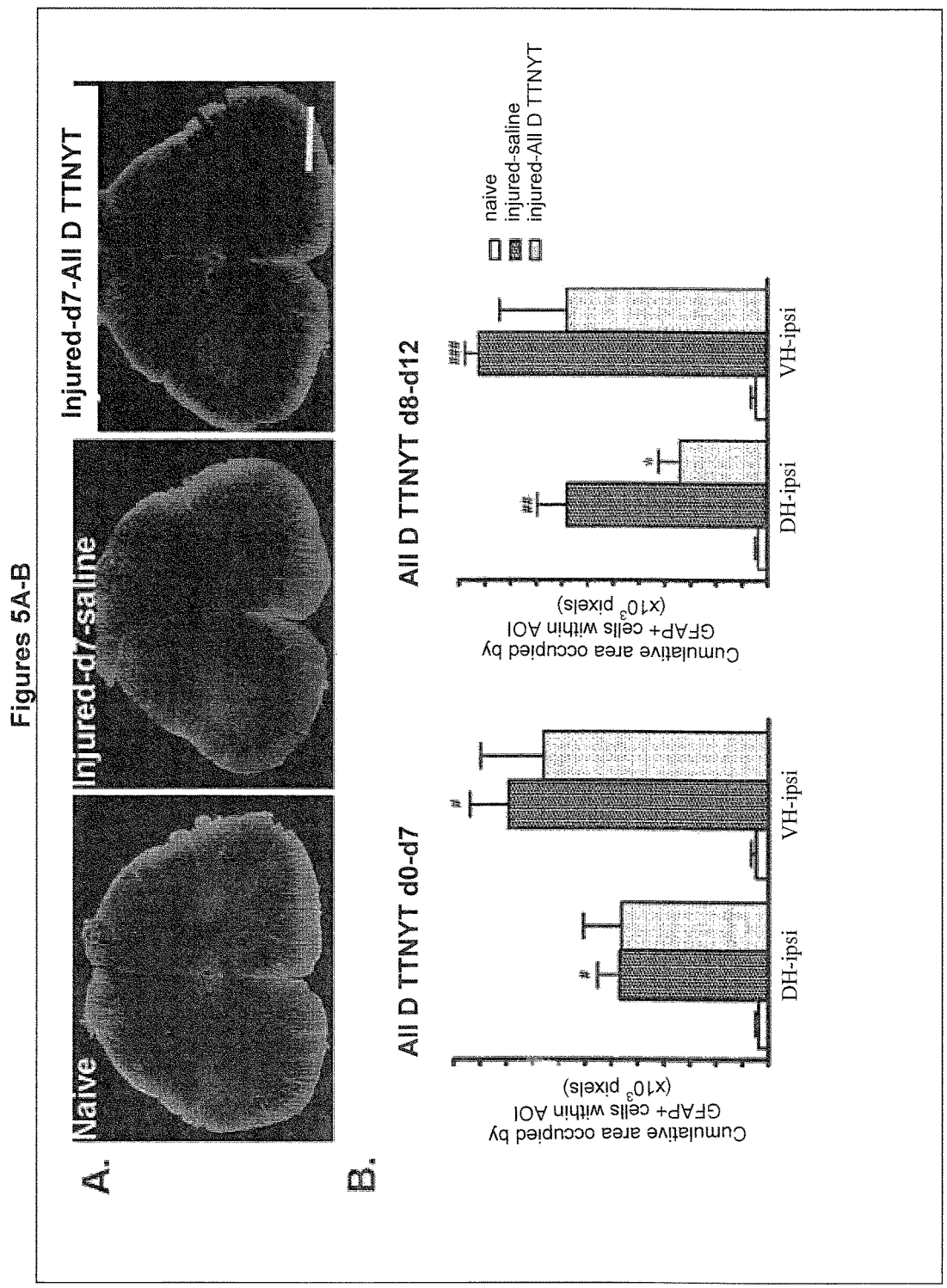

Figures 6A-B
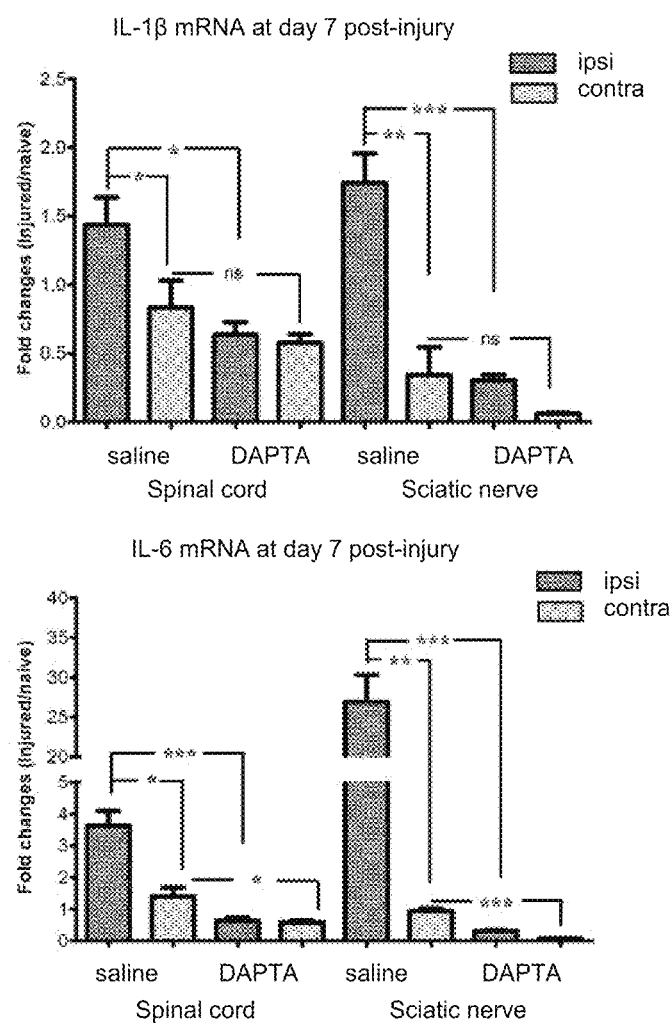

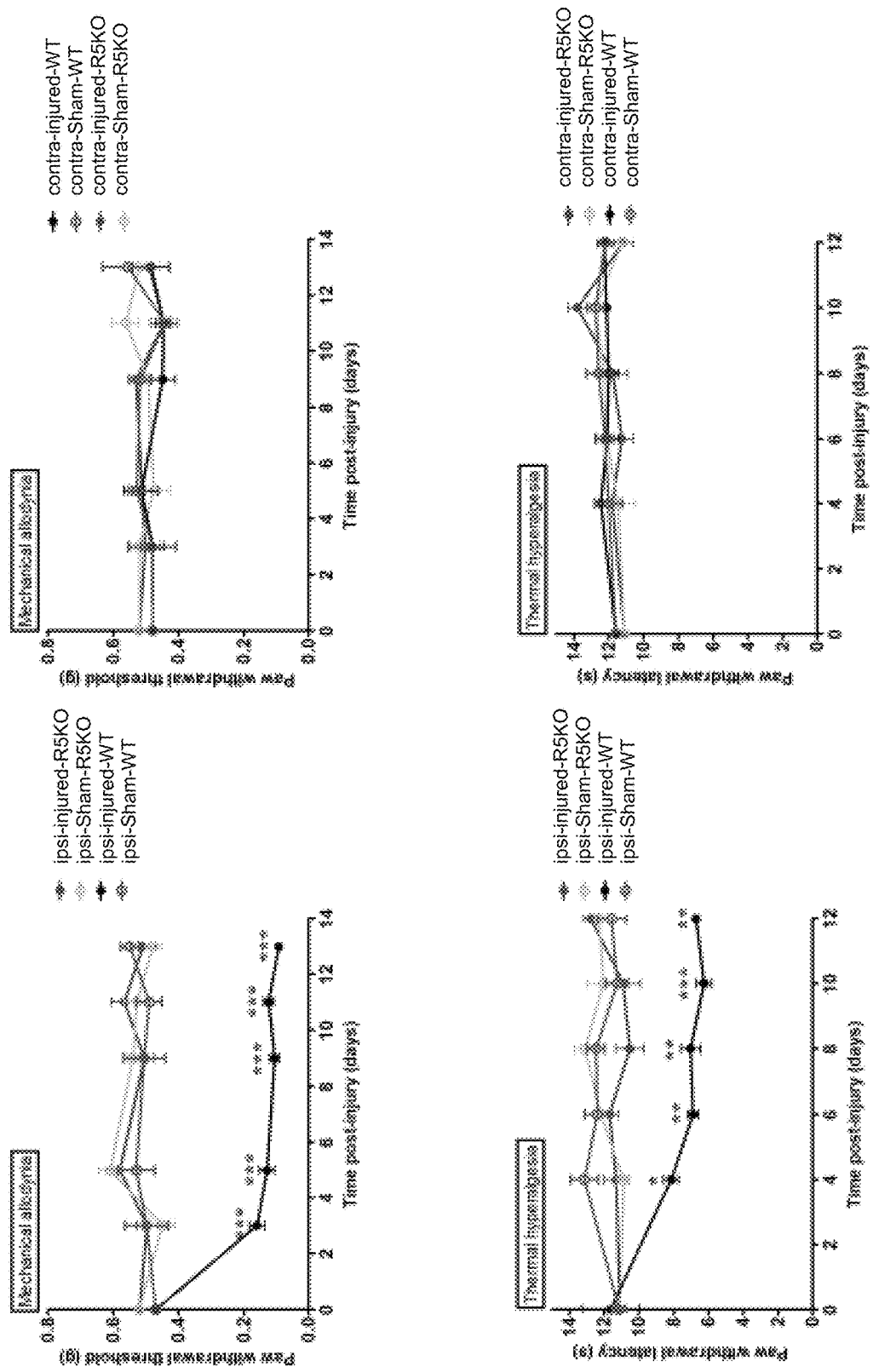
Figures 7A-D

Figures 8A-C
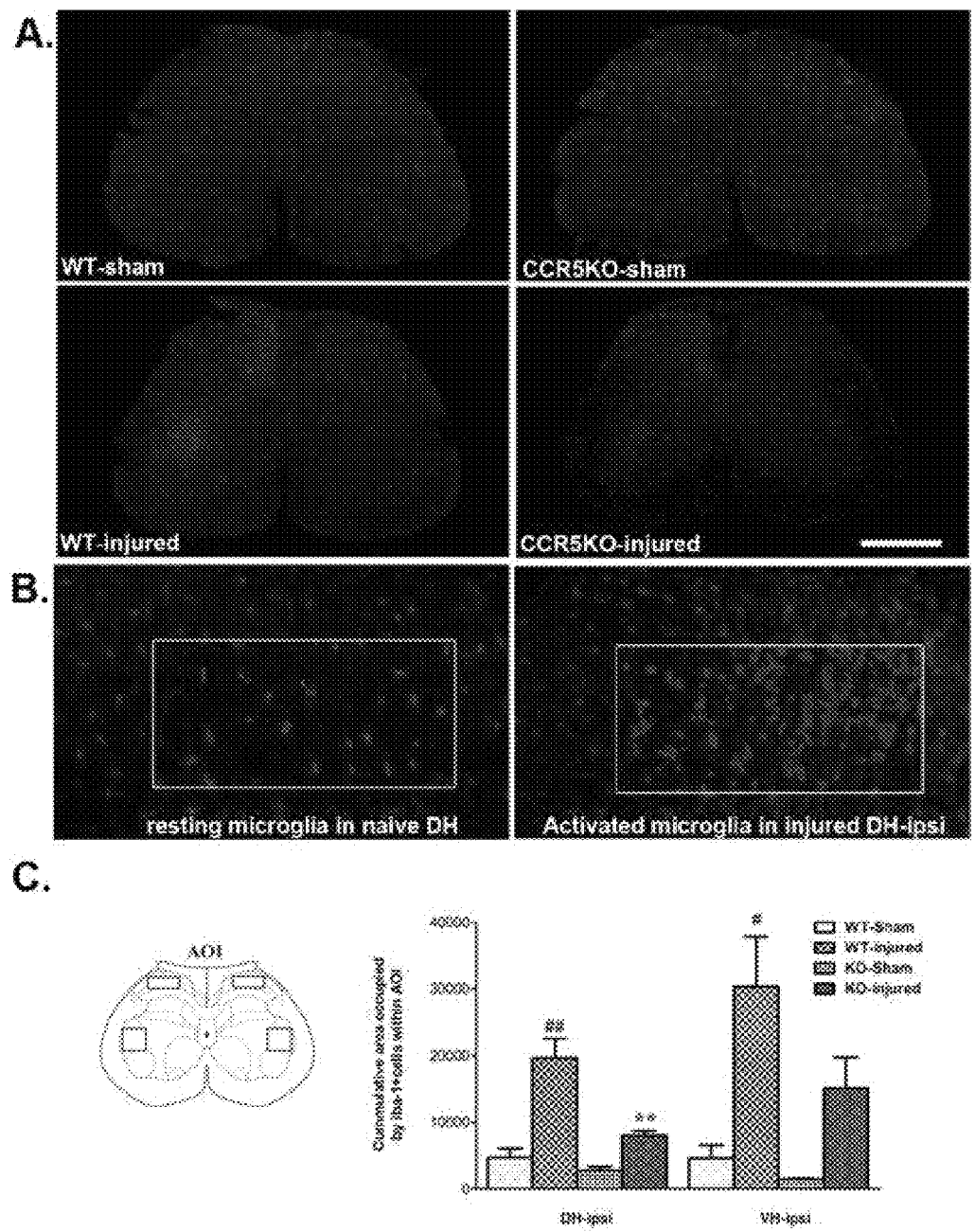

Figures 10A-D
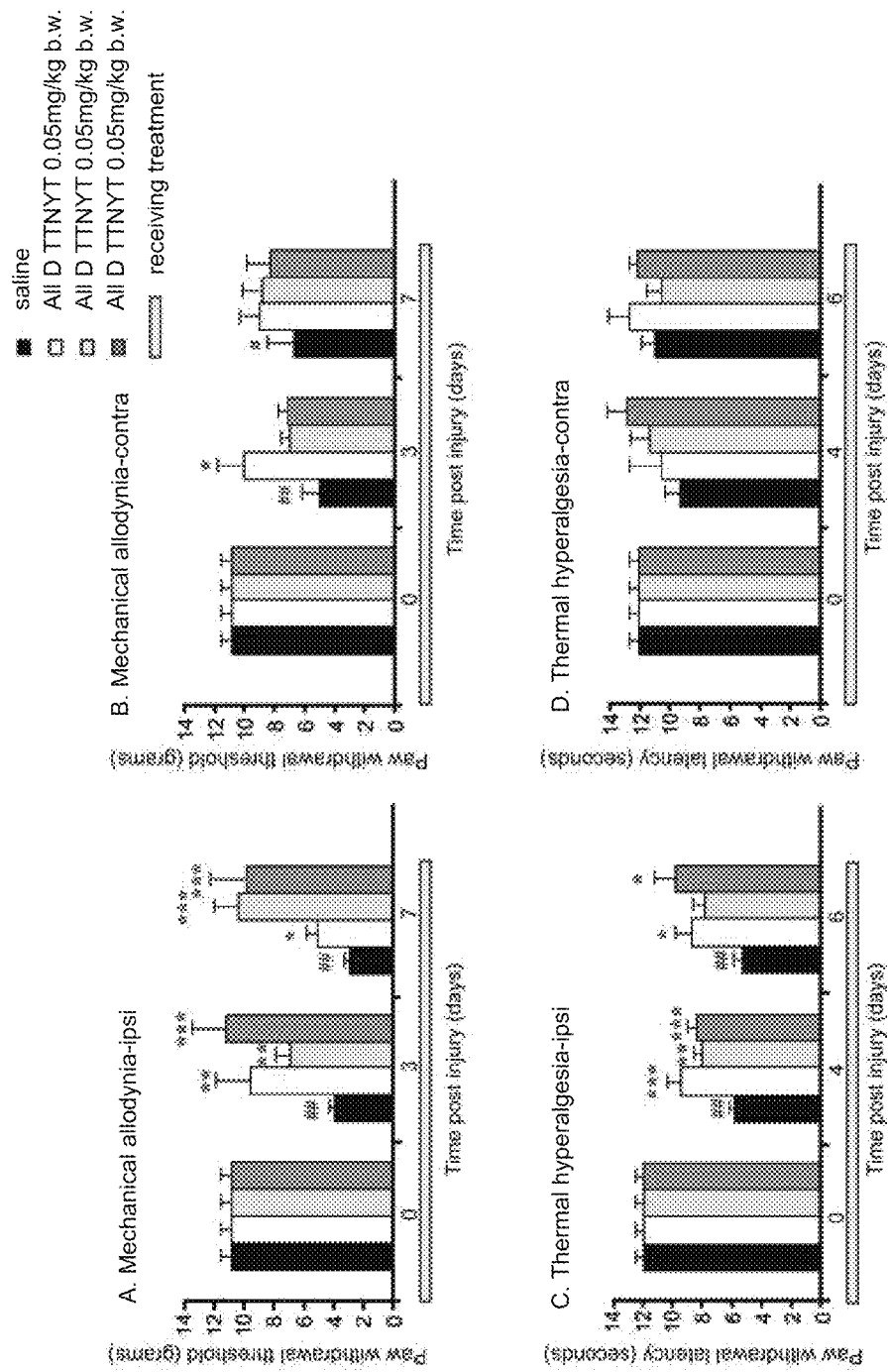

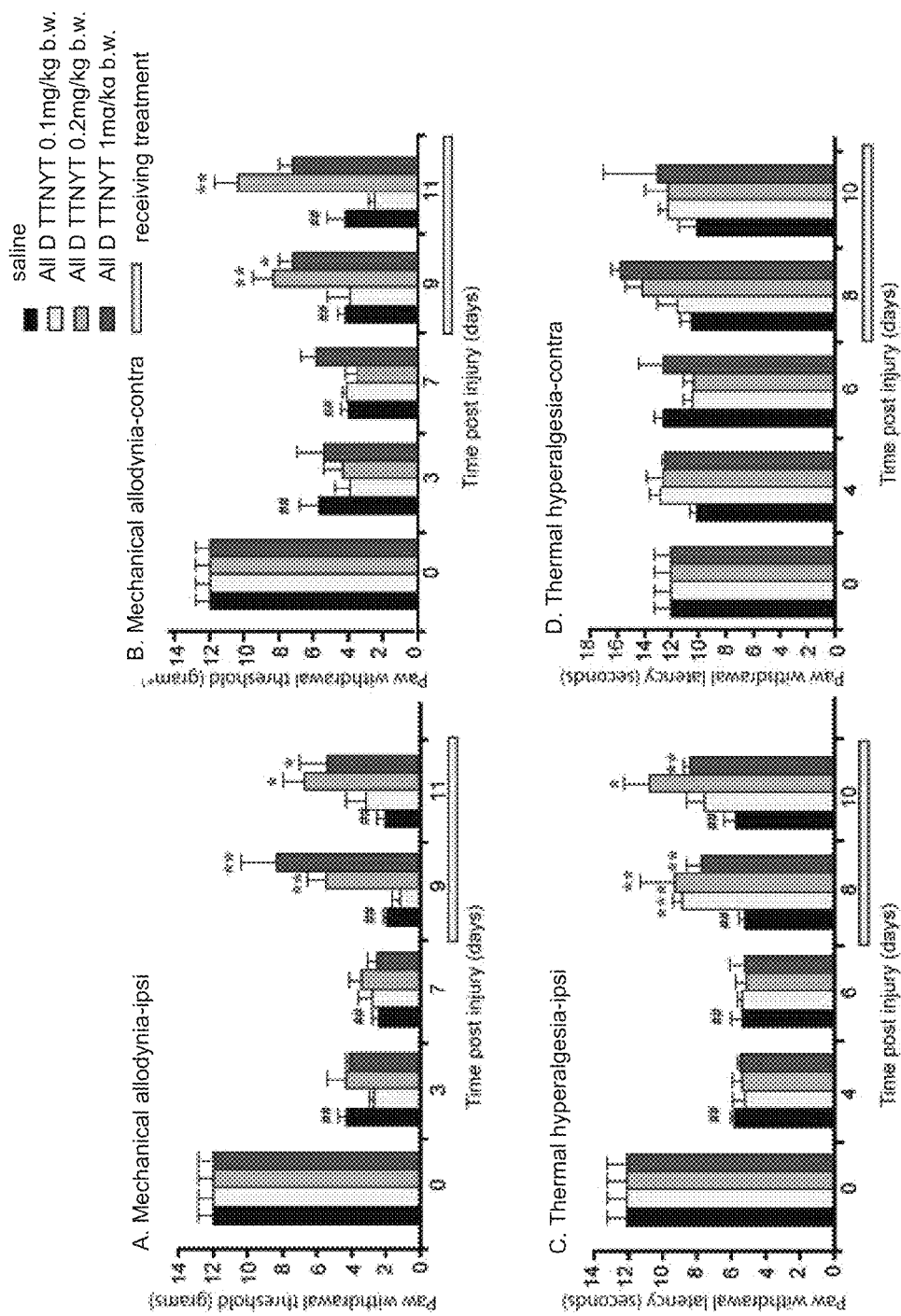
Figures 11A-D

Figures 12A-C
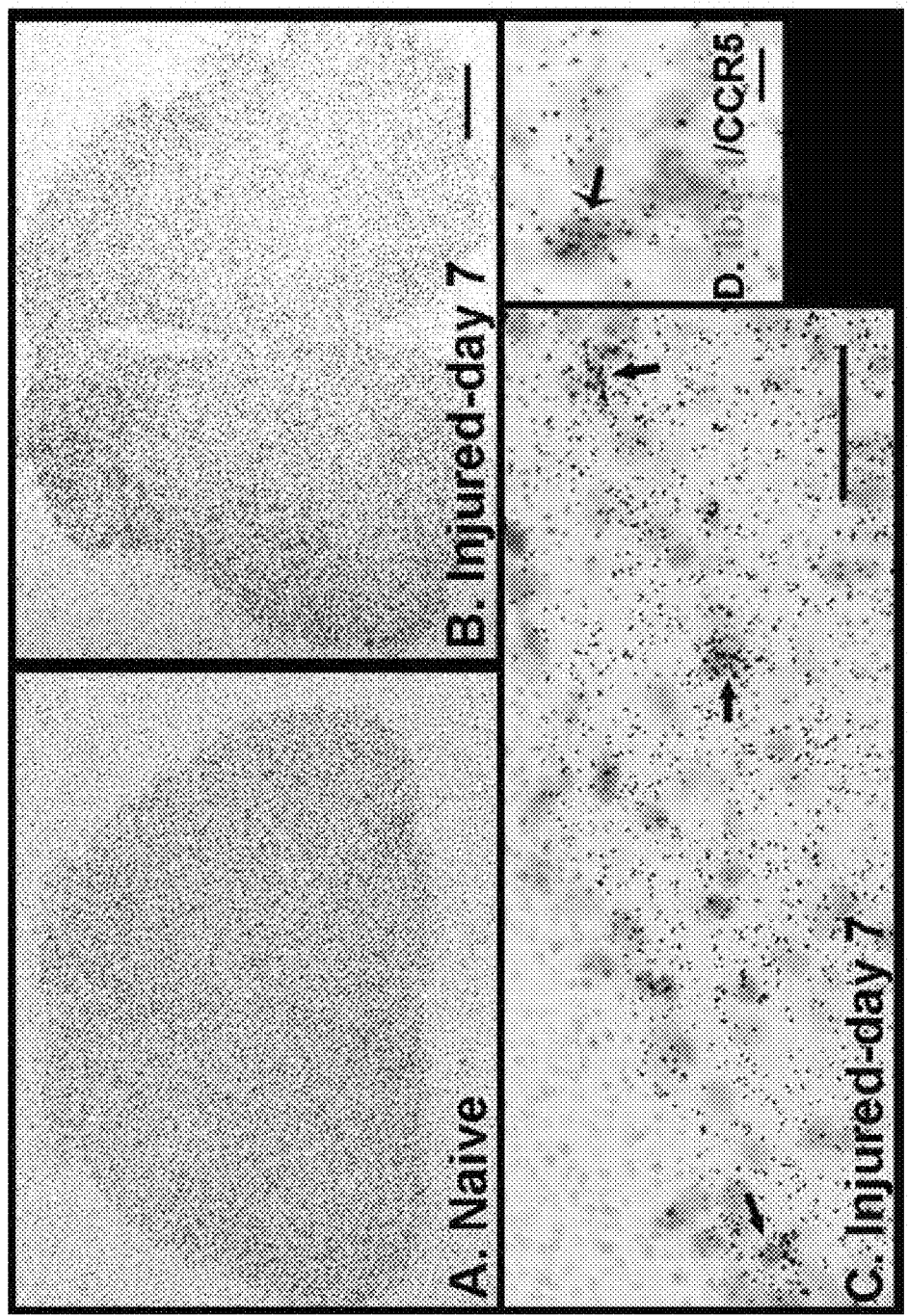

MODIFIED PEPTIDE THAT REDUCES PAIN IN PERIPHERAL NEUROPATHY

INTRODUCTION

Neuropathic pain is a sensory disorder that results from damage or dysfunction of peripheral and/or central neuronal pathways through injury, cancer, diabetes, or infection. It is characterized by spontaneous and/or abnormal stimulus-evoked pain, such as allodynia (pain sensation evoked by normally innocuous stimuli) and/or hyperalgesia (increased pain intensity evoked by normally painful stimuli). Millions of people worldwide suffer from this disorder. Unfortunately, many forms of neuropathic pain cannot be adequately treated using conventional analgesics. For decades, pain modulation have been viewed as being mediated solely by neurons. Increasing evidence strongly suggests active involvement of glial cells and an inflammatory reaction, including chemokine signaling in the pathogenesis. The hypersensitive state experienced by individuals suffering from neuropathic pain involves spinal microgliosis which is not just a property of those cells already existing in the spinal cord, but also those coming from chemokine mediated proliferation and recruitment of blood-born macrophages and myeloid stem cells in the bone marrow (Zhang, et al., J. of Neurosci., 2007). All D:TTNYT (SEQ ID NO:1) will undergo further testing as a potential therapeutic for neuropathic pain.

Chemokine receptors CCR2, CCR5 and their ligands have been found in glia and neurons, respectively, following nerve injury. Receptor antagonist, DAPTA, an octapeptide derived from HIV gp120, dramatically blocks neuroinflammation in three different rat models (Socci, Peptides, 1996; Rosi, Neuroscience 2005)

The mechanism probably includes its ability to block CCR5 and CCR2 receptor-mediated monocyte chemotaxis and transformation into intravascular macrophages en route to the brain, as well as recruitment and activation of microglial cells and other progenitor cells. In any case, of the hundreds of HIV gp120 derived pentapeptide analogs of DAPTA identified and synthesized in our lab, all of them have potent CCR2 and CCR5 antagonist activity. It is logical that the HIV virus has evolved many sequences to evade immune surveillance all of which bind tightly to receptors on rapidly expanding and/or readily activated cells like monocytic stem cells DAPTA reduces microglial and astrocyte activation in an inflammatory rat model of Alzheimer's disease. In this application, we sought to investigate All D:TTNYT (SEQ ID NO:1), an analog of DAPTA in which all five amino acid residues are the "D" stereo isomers rather than the naturally occurring "L" stereo isomers. The purpose of the investigation was to determine whether All D:TTNYT (SEQ ID NO:1) is efficient in preventing and/or relieving nerve injury induced chronic pain by targeting activated spinal microglia/astrocytes and related inflammatory response.

BACKGROUND

Large peptides called chemokines not only orchestrate chemotaxis in immune cells, but also are involved in neurodevelopment and neurophysiological signaling in brain. Chemokines have recently been recognized as essential elements in numerous neurodegenerative diseases and related neuroinflammation. In particular, recruitment of "activated" peripheral blood monocytes containing CCR5 chemokine receptors into atherosclerotic and other types of neuropathological plaques is pivotal to a number of diseases with neuroinflammatory etiologies including HIV and other dementias.

The CCR5 or R5 receptor became the focus of much attention when it was shown to be the essential receptor to which HIV must bind before it enters and infects cells; virtually all "founder" viruses, clones of the actual disease-transmitting virus, use CCR5 exclusively as an entry protein. The drug receptor for DAPTA (D-Ala-Peptide T-amide), the first HIV receptor blocker and entry inhibitor, has been proven to be CCR5 (Polianova, et al., Antiviral Research, 2005).

A number of short enzyme-resistant peptide analogs have been developed which also act as antagonists of CCR2 and CCR5, blocking binding of free HIV envelop proteins (gp120) and receptor signaling, now understood to be causes of immune and CNS inflammatory pathogenesis. Even when plasma HIV is undetectable, the viral "reservoir" of persistently infected cells, now identified as monocytes, continues to release highly potent, receptor active gp120 which drives pathogenesis.

Monomeric DAPTA (M-DAPTA or Adaptavir®) is a third generation HIV receptor blocker antiviral currently in Phase II studies in healthy patients with no detectable HIV-plasma virus as the result of being treated with and maintained on various cocktails of anti-retroviral therapeutics; m-DAPTA, which has been manufactured and formulated to avoid its tendency to form biologically inactive aggregates, has an extremely high (femtomolar range) affinity for R5. The primary endpoint of the ongoing trial is the previously observed (Polianova et al., Peptides, 2003) gradual reduction of infectious virus in white blood cells to undetectable levels in most patients by six months. The secondary endpoints include the serum levels of a number of inflammatory and anti-inflammatory cytokines to replicate a previous clinical study (Ruff, et al., Current HIV Research, 2003) which showed that DAPTA significantly reduced 4 inflammatory cytokines and increased 4 anti-inflammatory cytokines. M-DAPTA, was previously shown to block activated microglial cells and NFkB activation in rats infused intraventricularly with endotoxin (Rosi, et al., Neuroscience, 2005), a model of inflammatory pathogenesis in Alzheimer's Disease.

While disputed by most investigators, the inventors believe their observations make clear that neuroinflammation lies at the root of many diseases of unknown etiology and is initiated in one or more of three ways: 1) viral/microbial infection, 2) tissue trauma/injury or 3) environmental toxin exposure. The actual form the neuroinflammatory disease takes is a function of time and location. With respect to time, inflammation early in pregnancy, for example, can lead to autism; inflammation later in pregnancy, to schizophrenia; and inflammation after 65 years, to Alzheimer's. With respect to location, optic nerve inflammation can lead to demylination in multiple sclerosis; in spinal cord to Lou Gehrig' disease; in the substantia nigra of the brain to Parkinson's disease; in joints, to arthritis, etc.

BRIEF DESCRIPTION OF THE DRAWINGS

FIGS. 2A-B illustrate pain preventive effects of All D TTNYT (SEQ ID NO:1) treatment on rats as measured by mechanical allodynia and thermal hyperalgesia.

FIGS. 3A-B illustrate pain reversal effects of All D TTNYT (SEQ ID NO:1) treatment on rats as measured by mechanical allodynia and thermal hyperalgesia.

FIGS. 4A-D: A: Photomicrographs depicting Iba-1 labeling in lumbar spinal cord sections 7 days after nerve injury. Partial sciatic nerve ligation induced a marked increase of Iba-1 immunoreactivity at the ipsilateral DH and VH of spinal cord as compared to that of naïve animals. Following administration of All D TTNYT (SEQ ID NO:1) (1 mg/kg, p.o., for one week) started immediately after nerve injury reduced Iba-1 ir in spinal microglial cells. High magnification images demonstrated multidimensional changes of activated microglia (ipsilateral), including cell density, cell shape/size and Iba-1 ir intensity, which were prevented by All D TTNYT (SEQ ID NO:1) treatment. Scale bar: 500 µm in the upper panel and 20 µm in the lower panel. B. Quantitative analysis using the same method described in FIG. 2B showing a significant increase of area occupied Iba-1$^+$ cells within a specific AOI following nerve injury, which was strikingly reduced following All D TTNYT (SEQ ID NO:1) treatment in both prevention and reversal paradigms. Data represents means±SEM. : $p<0.01$, *: $p<0.001$, All D TTNYT (SEQ ID NO:1) vs. saline in their respective regions. ##: $p<0.01$, ###: $p<0.01$, naïve vs. injured in their respective regions. n=3-4 animals per group and 5-6 sections per region. C. Fourteen days after nerve injury, bone marrow derived GFP$^+$ monocytes/macrophages accumulated in the ipsilateral side DH and VH, which was completely abolished at the presence of All D TTNYT (1 mg/kg b.w., p.o. d0-d14). Scale bar: 500 µm. D. Number of ramified GFP$^+$ cells within the spinal cord parenchyma was significantly lower in All D TTNYT (SEQ ID NO:1) treated animals than those received saline treatment. Data represent Mean±SEM. : $p<0.01$, *: $p<0.001$, All D TTNYT (SEQ ID NO:1) vs. saline in their respective regions.

FIGS. 5A-B: A: Photomicrographs depicting GFAP labeling in lumbar spinal cord sections 7 days after nerve injury. To compare with naïve animals, partial sciatic nerve ligation strikingly increased GFAP immunoreactivity at the ipsilateral DH and VH of spinal cord. This increase was not significantly affected by All D TTNYT (SEQ ID NO:1) treatment (1 mg/kg, p.o., for one week) started immediately after nerve injury. B: Quantification analysis demonstrating that the cumulative area of GFAP$^+$ cells within a defined AOI were markedly increased at days 7 and 12 post-injury as compared to that of naïve animals at the same time points. All D TTNYT (SEQ ID NO:1) preventive treatment had no effect; however, reversal treatment partially reduced the magnitude on the increase of surface occupied by GFAP$^+$ cells. Data represents means±SEM. ##: $p<0.01$, ###: $p<0.01$, naïve vs. injured in their respective regions. Data represent Mean±SEM. *: $p<0.05$ All D TTNYT (SEQ ID NO:1) vs. saline in their respective regions. Scale bar: 500 µm. n=3-4 animals per group and 5-6 sections per region.

FIGS. 6A-B: To compare with naïve animals, partial sciatic nerve injury induced an inflammatory reaction within the spinal cord and in damaged nerves by manifold increase in levels of IL-1β and IL-6 at the ipsilateral side. Administration of All D TTNYT (SEQ ID NO:1) (1 mg/kg, p.o.) for one week started immediately after nerve injury significantly reduced inflammatory response by reducing the increase of IL-1β and IL-6 expression. Data represents means±SEM. *: $p<0.05$, : $p<0.01$, *: $p<0.001$.

FIGS. 7A-D: Following partial ligation on the sciatic nerve, paw withdrawal thresholds and latencies remained at the same levels as before surgery in CCR5 KO mice, while in wild-type mice, injured paw withdrawal thresholds to von Frey stimulation decreased sharply from 0.54±0.06 g before surgery to 0.09±0.01 g two weeks after injury and withdrawal latencies to heat stimulation decreased also from 11.36±1.089 s before surgery to 6.73±0.27 s at day 14 post-injury. Data are shown as mean±SEM; : $p<0.01$, *: $p<0.001$; n=4-6 mice/group. Baseline data (day 0) was obtained by an average of 2 measurements, 1-2 days before surgery.

FIG. 8A-C. A. Peripheral nerve injury induced spinal microglial activation observed in wild type mice was significantly impaired in CCR5 KO mice. B. Methodology for the quantitative evaluation on spinal microglial activation. A threshold of fluorescence intensity for Iba-1 was established according to the signals on naïve animals. All objects within the AOI having fluorescence intensity above the chosen threshold were considered as parts of Iba-1 positive cells and were subject to the quantitative analysis. C. Quantitative analysis based on the cumulative area occupied by Iba-1+ cells showed an impairment of microglial activation in CCR5 KO mice. Data are shown as mean±SEM; #: $p<0.05$, ##: $p<0.01$, injured vs sham; **: $p<0.01$, wt vs KO mice; n=3-5 section/mouse, n=4 mice/group. Scale bar=500 µm FIG. 9 Monocytes were treated with the indicated doses of All D TTNYT (SEQ ID NO:1) for 30 minutes prior to chemotaxis against human MCP-1 or MIP-1β (both 50 ng/ml) for 90 minutes. Data is the average of two separate experiments, conducted with triplicate determinations. Data (chemotactic index) are presented as Mean±SEM. The IC$_{50}$ for inhibition of MCP-1 or MIP-1β was generated using a nonlinear inhibition curve fit in GraphPad Prism Version 5.0. The chemotactic index for MCP-1 was 2.5-3.5, while for MIP-1β it was approximately 2.

FIG. 10A-D. Nerve injured rats treated with saline developed a bilateral hypersensitivity to mechanical stimuli (A-B) and a unilateral hypersensitivity to thermal stimuli (C-D) resulting in allodynia and hyperalgesia, respectively. Oral administration of All D TTNYT (SEQ ID NO:1) (0.05, 0.1, or 1 mg/kg, p.o., d0-d7) to nerve-injured rats completely prevented the development of mechanical allodynia (A-B) and attenuated the initiation of thermal hyperalgesia (C). Nociceptive behavior in All D TTNYT (SEQ ID NO:1) treated group and saline treated controls differed significantly at each time point, *: $p<0.05$, : $p<0.01$, *: $p<0.001$. Following injury, paw withdrawal responses in animals subjected to saline treatment were significantly different from day 0 pre-injury baseline responses (#: $p<0.05$, ##: $p<0.01$). Data represent Mean±SEM. n=4 per group.

FIG. 11A-D. Animals started to receive All D TTNYT (SEQ ID NO:1) or saline on day 8 and continued for 4 days post-injury where both paw withdrawal thresholds (A) and latencies (C) in response to mechanical and thermal stimuli, respectively, had reached their lowest level indicative of well established hypersensitivity. Oral administration of All D TTNYT (SEQ ID NO:1) (0.1, 0.2, and 1 mg/kg) to nerve-injured rats resulted in a bilateral increase of mechanical threshold (A-B) and unilateral increase of thermal latency (C-D) to elicit a paw withdrawal response compared to saline treated animals indicating reversal of existing hypersensitivity. Nociceptive behavior in All D TTNYT (SEQ ID NO:1) treated group and saline treated controls differed significantly at each time point, *: $p<0.05$, : $p<0.01$, *: $p<0.001$. Following injury, paw withdrawal responses in animals subjected to saline treatment were significantly different from day 0 pre-injury baseline responses (##: $p<0.01$). Data represent means±SEM. n=3-5 per group.

FIG. 12A-C. The expression of constitutive CCR5 mRNAs was not detected within the spinal cords of control animals (A). Following nerve injury, up-regulation of CCR5 transcripts at both dorsal and ventral horns of spinal cord, ipsilateral to the nerve injury was observed (B: highlighted areas). High magnification microscopic analysis revealed that positive signals (silver grains) for CCR5 mRNAs were observed on thionine stained small cell bodies (black arrows), presumably some glial cells within both dorsal and ventral horns (C). Double labeling studies confirmed that the receptor transcripts expressing cells were Iba-1 positive activated microglia (D). Scale bar: 100 µm.

MATERIALS AND METHODS

Tissue Preparation

Figure 1:
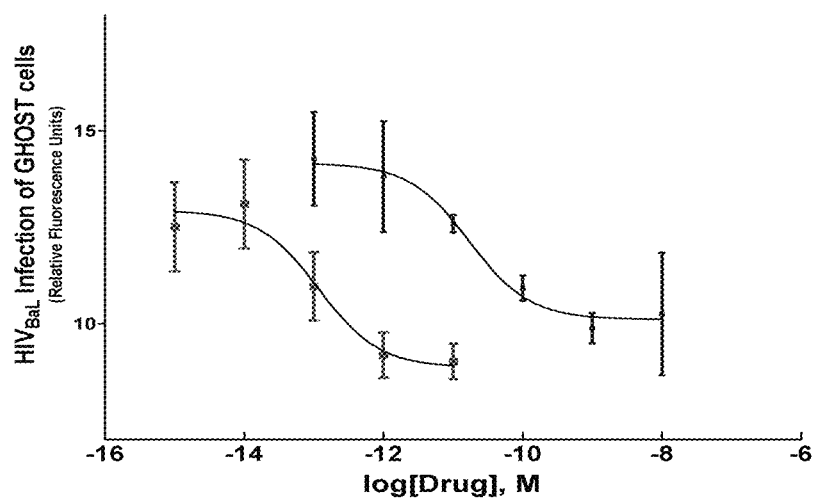
FIG. 1 shows DAPTA and All D TTNYT (SEQ ID NO:1) block CCR5 receptors as measured by the ability of both peptides to block infection of a virus ($HIV_{Bal}$). This virus uses CCR5 receptor binding to infect its host cell.

Unilateral partial ligation of the sciatic nerve causing partial injury of somatosensory fibers with a rapid and long-lasting hypersensitivity (allodynia and hyperalgesia) is a rat model of human neuropathy. Before and one week following surgery, mechanical hypersensitivity was assessed using a series of calibrated von Frey monofilaments according to Chaplan; the 50% response threshold was calculated using Dixon's up-down method. Thermal hyperalgesia was measured using Hargreaves' paw withdrawal test with a focused high-intensity projector lamp.

For Histological Studies

Rats and mice were deeply anaesthetized with ketamine/xylazine and then perfused transcardially with 0.9% saline followed by 4% paraformaldehyde (PFA) in 0.1 M sodium phosphate buffer (pH 7.4). The ipsi and contralateral L4-L6 DRGs from rats, as well as the corresponding levels of the spinal cords from both rats and mice were removed and placed in the same fixative overnight, then transferred to 30% sucrose for cryoprotection. Frozen spinal cords were cut transversely into 30 µm thick sections on a sliding microtome, collected in an antifreeze solution and stored at −20° C. until use. The DRG were embedded in OCT compound (Tissue Tek, Miles Laboratories, Elkhart, USA), cut longitudinally into 14 µm thickness in a cryostat (Microm, Heildeberg, Germany), mounted onto Superfrost Plus slides, and stored at −80° C. until use.

For Real Time PCR Experiments

Seven days after the nerve ligation, rats were deeply anaesthetized with isoflurane and decapitated. Lumbar (L4-L6) spinal cords and sciatic nerves were quickly removed and then snap frozen in liquid nitrogen and stored at −80° C. until use.

In Vitro CCR5 Receptor Viral Infectivity Assay

Reporter cells (GHOST R5) were allowed to attach in a 96 well plate for 3.5 hr then various concentrations of drugs (DAPTA and All D:TTNYT (SEQ ID NO:1)) were added in media replacement. A CCR5-specific virus (HIVBaL) was added 1 hr later. CCR5 receptor viral infectivity was tested on CCR5-containing cells with a Green Fluorescent Protein (GFP) reporter that responds to viral infection.

Nerve Injury Model

A partial ligation on the left sciatic nerve was conducted in adult male rats (Seltzer model).

All D:TTNYT (SEQ ID NO:1) Treatment Paradigms

Prevention: d0-d7 post-injury, 0.05, 0.1, 1 mg/kg daily p.o.

Reversal: d8-d12 post-injury, 0.1, 0.2, 1 mg/kg daily p.o.

Pain Behavioral Testing

Mechanical allodynia and of hind paw were measured with Von Frey Hairs (Chaplan et al., 1994)

Thermal hyperalgesia was measured in response to steady heat beam, by using Hargreaves apparatus (Hargreaves et al., 1988)

Immunohistochemistry

Iba-1 and GFAP were used as markers for microglia and astrocyte respectively to monitor glial response to nerve injury and to All D:TTNYT (SEQ ID NO:1) treatment. Image analysis was performed with a fluorescence microscope equipped with a digital camera.

Real Time PCR

Quantitative real time-PCR was performed to detect changes of IL-1b and IL-6 mRNA within the spinal cord.

Statistic Analysis

Statistical analyses of the results were made with Student's t-test or one-way ANOVA followed by Dunnett's case-comparison posthoc test.

Animals

Animals were acclimatized to standard laboratory conditions (14 h light, 10 h dark cycle) and given free access to rat chow and water. Adult male Sprague-Dawley rats (Charles River, Quebec, Canada) were used and weighed 250-275 g at the time of surgery. GFP$^+$ chimeric mice were obtained from the CHUL Research Center, Laval University (Dr. S Rivest). Adult male CCR5 knock-out mice (B6.129p2-CCR5 tm1kuz/J) were purchased from Jackson lab (Bar Harbor, Me., USA). All protocols were performed in accordance with guidelines from the Canadian Council on Animal Care and were approved by the McGill University and Laval University Animal care Committees.

Peptides and Chemotaxis Assay

All D TTNYT (SEQ ID NO:1) (synthesized by RAPID Laboratories) was purified to >95% homogeneity and verified by HPLC isolation, amino acid analysis, and mass spectroscopy. Peptides were dissolved in sterile water and stored as frozen (−20° C.) aliquots at 0.1 mM until use.

Chemotaxis was assayed in 96-well plates (NeuroProbe, Cabin John, Md.) with 5 µM pore size, PVP-free membranes. Purified human monocytes (>95%) prepared from healthy adult human donors by centrifugal elutriation (>95% pure, gift of L Wahl, NIDR, NIH) were resuspended in chemotaxis assay buffer (DMEM supplemented with 0.1% BSA) at a density of 2×10$^6$ cells/ml. Cells were labelled with 1.0 µM Calcein AM (Invitrogen) for 30 minutes at 37° C., 5% CO2. Following incubation, cells were washed once and resuspended in chemotaxis assay buffer (DMEM, 1 mg/ml BSA, 25 mM Hepes) at a density of 2×10$^6$ cells/ml. Cells were then further treated with the indicated concentrations of All D TTNYT (SEQ ID NO:1) for 30 minutes at 37° C. Lower wells were filled with either buffer, MCP-1 or MIP-1β (PeproTech) as test chemoattractants. The filter plate was snapped on and monocytes which had been treated with All D TTNYT (SEQ ID NO:1) or buffer only (30 min, 37° C.) were loaded onto the upper filter surface (50,000 cells in 25 µl). Chambers were then incubated at 37° C. for 90 minutes. At the conclusion of the test period, non-migrating cells were wiped off the upper filter surface and relative fluorescence units (RFUs) of the migrating cells from the lower surface determined by bottom reading in a spectrometer (M5 SpectraMax) at 485/530 nm (Ex/Em). Triplicate determinations were made and results are expressed as the mean Chemotactic Index, the ratio of cell migration of the indicated chemokine compared to cells that had been treated with the indicated dose of All D TTNYT (SEQ ID NO:1), of two independent determinations.

Animal Model of Neuropathic Pain

The current project uses the well established rat neuropathic pain model described by Seltzer et al [27]. Under anesthesia of isoflurane, the left common sciatic nerve was exposed via blunt dissection through the biceps femoris muscle. The dorsum of the nerve was carefully freed from surrounding connective tissues at a site near the trochanter. A 6-0 suture was inserted into the nerve with a ⅜ curved, reversed-cutting mini-needle (Tyco Health Care, Ontario, Canada) and tightly ligated so that the dorsal one-third to one-half of the nerve thickness was trapped in the ligature. The muscle and skin layers were closed with two muscle sutures (4-0) and three to four skin sutures (4-0). Sham-operated rats underwent the same surgical procedure but the nerve was exposed and left intact. Survival times were 7 and 12 days post-surgery. A group of naive rats was included in the protocol to obtain basal levels of certain gene and protein expression.

The partial ligation was also performed on the left sciatic nerve of GFP+ chimeric mice (10 weeks after irradiation and bone marrow transplantation) and CCR5 knock-out mice, according to the method described by Malmberg and Basbaum [15]. All mice were kept for 14 days.

Treatment Paradigms

Prevention:

To investigate whether blockade of both CCR2 and CCR5 can prevent the development of behavioral hypersensitivity following nerve injury, a set of rats were treated with saline or All D TTNYT (SEQ ID NO:1) (0.05, 0.1 or 1 mg/kg b.w, p.o.) administered immediately after surgery and continued once daily for 7 days following nerve injury (n=4 for saline and n=4 for All D TTNYT (SEQ ID NO:1)/each dose).

Reversal:

To further ascertain whether blockade of both CCR2 and CCR5 could also reverse already established neuropathic hypersensitivity, saline or All D TTNYT (SEQ ID NO:1) (0.1, 0.2 or 1 mg/kg b.w., p.o.) was administered to separate groups of rats starting from day 8 post-injury, when both mechanical allodynia and thermal hyperalgesia had reached their lowest level. The treatment lasted for 4 days (day 8-12) (n=5 for saline and n=4-8 for All D TTNYT (SEQ ID NO:1)/each dose).

A group of GFP+ chimeric mice received All D TTNYT (SEQ ID NO:1) or saline treatment (day 0-day 14, 1 mg/kg b.w., p.o.) to examine the effects of All D TTNYT (SEQ ID NO:1) in monocyte trafficking into the spinal cord (n=4/group)

Nociceptive Behavioral Testing

Both rats and mice subject for behavioral testing were habituated to the testing environment daily for at least two days before baseline testing. All animals were assessed for mechanical allodynia and thermal hyperalgesia of both hind paws before surgery and at specified time points after injury until they were sacrificed for histological studies. The behavioral tests started 3-4 hrs after the drug administration. The investigator was totally blinded to the treatments the rats received. Mechanical sensitivity was assessed using calibrated von Frey hairs as described by Chaplan et al [6]. Animals were placed in boxes on an elevated metal mesh floor and allowed 40 to 60 min for habituation before testing. A series of von Frey filaments with logarithmically incrementing stiffness (Stoelting) was applied perpendicular to the mid-plantar region of the hind paw. The 50% paw withdrawal threshold was determined using Dixon's up-down method as previously described [9]. Thermal hyperalgesia was measured using paw withdrawal test. Animals were placed on a glass floor within Plexiglass cubicles. After habituation, a focused high-intensity projector lamp was directed below onto the mid-plantar surface of the hind paw and reaction time (withdrawal latency of the hind paw) of the rat was recorded automatically [11]. The commercial device (IITC Model 336) was calibrated so that the pre-surgical baseline paw withdrawal latencies were approximately 10-12 sec. Twenty seconds was used as a cut-off time to avoid damage to the animal's skin. The measurements were repeated four times for rats and eight times for mice, at 3 min intervals on each paw. The initial pair of measurements was not used. The average of the three or seven remaining pairs of measurements was taken as data. Efficacy of All D TTNYT (SEQ ID NO:1) was determined according to the following formula: $Mean_{All\ D\ TTNYT} - Mean_{control\ (saline)}/Mean_{naive\ (baseline)} - Mean_{control\ (saline)} \times 100\%$.

In Situ Hybridization (ISH)

Detection of mRNAs encoding CCR5 was performed on lumbar spinal cord and DRG sections using 35S-labeled riboprobes. Radiolabeled CCR5 probe was synthesized with a 702 bp-cDNA cloned into expression vector pCR-Blunt II-TOPO. Sequence chosen was verified by BLAST analysis in GenBank. Hybridization were performed as per a previously described protocol [30]. Briefly, plasmids were linearized and sense and anti-sense cRNA probes were synthesized with appropriate RNA polymerase. Sections were postfixed in 4% PFA and digested by proteinase K (10 μg/ml), after which spinal cord sections were rinsed in water and by a solution of 0.1 M triethanolamine (TEA, pH 8.0), acetylated in 0.25% acetic anhydride in 0.1 M TEA and then dehydrated. Hybridization of the sections by riboprobe involved 90 μl hybridization mixture containing $10^6$ cpm/ml radioactivity and incubation at 55° C. overnight in a slide warmer. Slides were rinsed in standard saline citrate (1×SSC: 0.15 M NaCl, 15 mM trisodium citrate buffer, pH 7.0) and digested by RNase A at 37° C. (20 μg/ml), rinsed in descending concentrations of SSC, and dehydrated through graded concentrations of ethanol. Sections were exposed to x-ray film (BioMax, Kodak, Rochester, N.Y.) for 2-3 days and dipped in NTB2 nuclear emulsion (Kodak). Slides were kept at 4° C. for 3-5 weeks safe from light and developed in D19 developer (Kodak) and counterstained with thionine.

Combination of Immunohistochemistry with ISH

Immunohistochemistry was combined with ISH to determine whether CCR5 is expressed on microglia. Spinal cord sections were processed by the avidin-biotin method using peroxidase as a substrate. Rabbit anti-ionized calcium-binding adaptor molecule 1 (Iba-1) polyclonal antibody was used as a marker for microglia. Briefly, sections were incubated with rabbit Iba-1 polyclonal antibody (1:1000; Wako Chemicals, Richmond, Va.) at room temperature (21-23° C.) for 2 h, and followed by a 2 h incubation with a biotinylated secondary antibody (Vector Laboratories, Burlingham, Calif., USA), and before final incubation with an avidin-biotin-peroxidase complex (Vectostain ABC Elite Kit; Vector Laboratories). The stainings were visualized by reacting in 0.05% diaminobenzidine and 0.003% hydrogen peroxide. Thereafter, sections were mounted, desiccated, fixed in 4% PFA, and digested by proteinase K. Pre-hybridization, hybridization and post-hybridization steps were performed according to the above protocol, with shorter dehydration times in ascending alcohol to prevent decoloration of immunoreactive cells. The slides were dried, exposed and developed as described above.

Immunohistochemistry (IHC)

Regular immunofluorescent staining was performed to characterize the spinal glial cell reaction to peripheral nerve injury and to All D TTNYT (SEQ ID NO:1) treatment. Free-floating sections were incubated overnight at 4° C. with the following antibodies: rabbit anti-Iba-1 polyclonal antibody (for microglia, 1:1000; Wako Chemicals, Richmond, Va.); and rabbit anti-glial fibrillary acid protein (GFAP) polyclonal antibody (for astrocytes, 1:1000; DakoCytomation, Carpinteria, Calif.); followed by 60-min incubation at room temperature in fluorochrome-conjugated goat secondary antibody.

RNA Extraction and Real-Time Quantitative PCR

Total RNA was extracted from spinal cords and sciatic nerves using RNeasy lipid tissue mini kit (QIAGEN). Synthesis of cDNA from total RNA was performed with SuperScript VILO cDNA synthesis kit (Invitrogen). Primers were produced by QIAGEN QuantiTect (IL-1□-QT00181657, IL6-QT00182896, GAPDH-QT00199633). Spinal cords and sciatic nerves collected from the following groups were analyzed: 3 naive animals; 3 saline-treated animals and 4 All D TTNYT (SEQ ID NO:1)-treated animals. Experiments were performed in triplicate using the SYBR Green I Dye technology. Levels of target mRNAs were normalized to the housekeeping gene GAPDH. Fold changes versus naive animals in their respective ipsi and contralateral sides were analyzed using the comparative Ct (dCT) method [14].

Image Processing and Analysis

Figure 9:
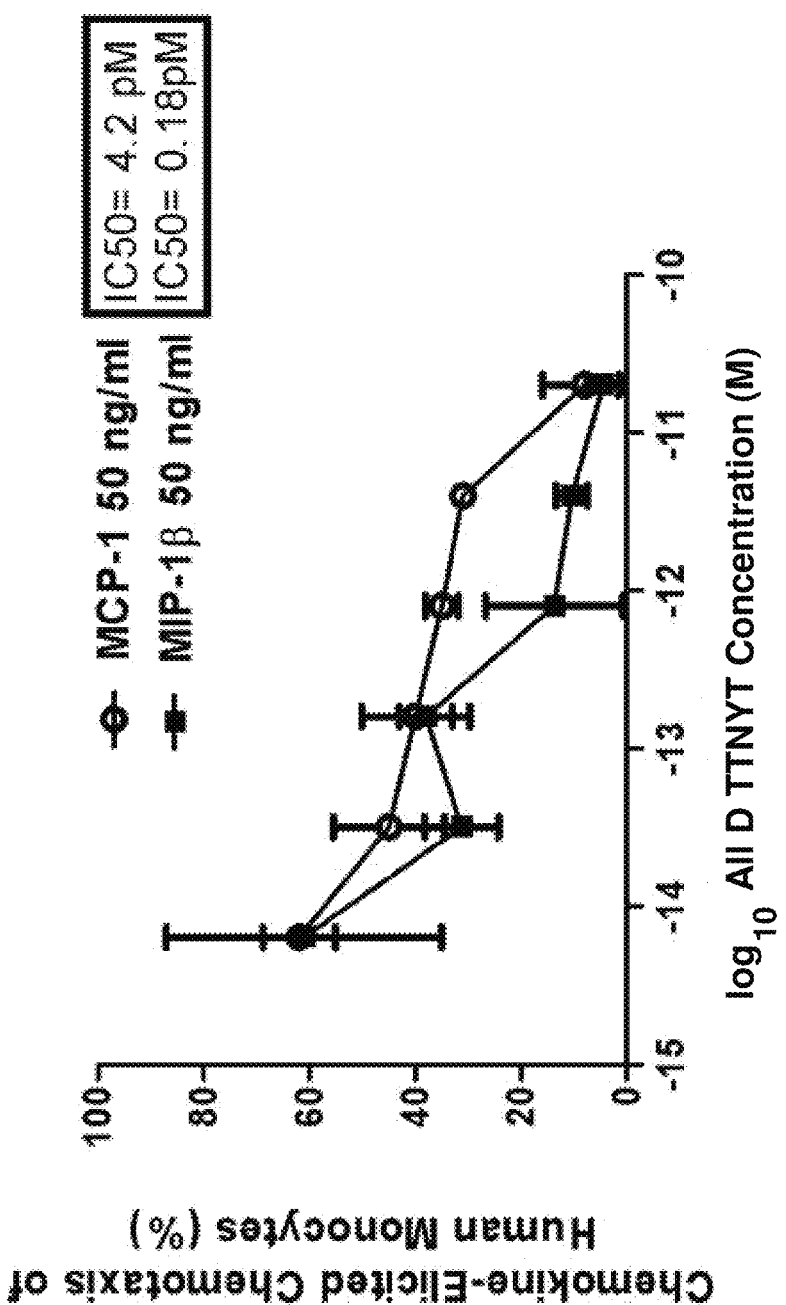

Images were acquired using an Olympus BX51 (Tokyo, Japan) microscope equipped with a color digital camera (Olympus DP71) and Olympus confocal laser-scanning biological microscope (Fluoview 1000). Quantitative analysis of both Iba-1 and GFAP staining was performed on images digitized using a constant set of parameters (exposure time, gain, and postimage processing) with special attention to avoid signal saturation. Four areas of interest (AOI) defined as: 2 rectangles on the dorsal horn (DH) (lamina I-III) and 2 rectangles on the ventral horn (VH) (lamina IX), on both sides relative to the side of injury, were selected. Two thresholds of fluorescence intensity for Iba-1 and GFAP respectively were established according to the signals on naïve animals. All objects within the AOI having fluorescence intensity above the chosen threshold were considered as parts of Iba-1 or GFAP positive cells and were subject to the quantitative analysis (FIG. 5B). We measured the area occupied by Iba-1+ or GFAP+ cells within the AOI by using Image Pro Plus 6.2 for Windows (Media Cybernetics Inc.) in different groups of animals: naïve (mice and rats), CCR5KO mice (sham and nerve injured), nerve injured rats treated with saline or treated with All D TTNYT (SEQ ID NO:1). Samples from 5-6 sections per animal and 3-4 animals per group were included for each quantitative analysis.

Statistical Analysis

All data are presented as mean±SEM. Statistic significance was determined using: 1) for behavioral analysis one way ANOVA followed by Dunnet's test for the changes of all time points vs. pre-surgery baseline; unpaired t-test for the difference between groups (All D TTNYT (SEQ ID NO:1)-treated vs. saline-treated at each time point); 2) unpaired t-test for the difference between groups in glial responses and in cytokine expression (CCR5 KO vs wild type, All D TTNYT (SEQ ID NO:1)-treated vs. saline-treated, injured saline treated vs naïve); 3) paired t-test for the difference between two sides (ipsi and contra) in cytokine expression. The criterion for statistical significance was $p<0.05$.

RESULTS

M-DAPTA attenuated pain in the paw of rats ipsilateral to experimentally inflicted nerve damage. All D:TTNYT (SEQ ID NO:1), can be shown to be a CCR5 antagonist that blocks infection of a CCR5 using virus, comparable to m-DAPTA, in blocking HIV infectivity. It not only prevents the development of nerve-injury induced neuropathic pain in both behavioral tests, but also reverses already established hypersensitivity. The behavioral outcomes probably resulted from inhibition of the inflammatory response following nerve lesion: cytokine changes in spinal cord and relevant peripheral nerve will be described in light of the histopathology and All D:TTNYT's (SEQ ID NO:1) chemokine antagonist properties. Details and other results are reported below.

1. Relative Antiviral In Vitro Potency of DAPTA & all D:TTNYT (SEQ ID NO:1) on CCR5 Receptors As illustrated in FIG. 1, monomeric DAPTA is represented by the large square symbols while All D:TTNYT (SEQ ID NO:1) is represented by the smaller symbols. The experiment, which was repeated 5 times in various cell systems, was performed in triplicate and bars correspond to standard error of the mean. Data were analyzed by a nonlinear fit using GraphPad Prism 5.

2. The CCR5 Receptor Antagonist, all D:TTNYT (SEQ ID NO:1), not Only Prevented the Development of Nerve Injury Induced Chronic Pain, but Also Reversed Established Hypersensitivity.

In a pilot study, we observed that 0.01 mg/kg of DAPTA inhibited neuropathic pain development (not shown). Our current experiments demonstrated that systemic administration of All D:TTNYT (SEQ ID NO:1) prevented the development of thermal hyperalgesia and mechanical allodynia following injury on the left sciatic nerve, which is effective at the dose of 0.1-1 mg/kg. All D:TTNYT (SEQ ID NO:1) also reversed already established mechanical and thermal hypersensitivity. The effect is more prominent with the dose of 0.2-1 mg/kg. N=4 per group, ##, $p<0.01$, injured vs baseline, *, $P<0.05$ All D:TTNYT vs saline; **$p<0.01$ All D:TTNYT vs saline.

3. All D:TTNYT (SEQ ID NO:1), Inhibited Nerve Injury Induced Spinal Glial Activation A. Microglia Reaction (Iba-1)

Nerve injury induced microglial activation in the ipsilateral side spinal cord, which was significantly reduced by the systemic administration of All D:TTNYT (SEQ ID NO:1). Note the difference of microglial cell size, shape, cell density and iba-1 ir intensity between the group of saline and All D:TTNYT (SEQ ID NO:1) treated animals.

B. Astrocyte Reaction (GFAP)

All D:TTNYT (SEQ ID NO:1) slightly inhibited nerve injury induced spinal astrocyte activation. The effect of All D:TTNYT (SEQ ID NO:1) on astrocytes was less evident than that of microglia.

4. All D:TTNYT (SEQ ID NO:1) Reduced Local Inflammatory Response within the Spinal Cord.

Following peripheral nerve injury, IL-1b and IL-6 mRNA in the ipsilateral spinal cord is increased. The difference between ipsi and contralateral sides was reduced with the treatment of All D:TTNYT (SEQ ID NO:1).

All D:TTNYT (SEQ ID NO:1) has been shown to prevent and reverse neuropathic pain and microglial activation after nerve injury fed to rats in a model where pathogenesis has been shown to be CCR2 dependent.

5. All D TTNYT (SEQ ID NO:1) Blocked CCR2 and CCR5 Mediated Human Monocyte Chemotaxis Where pathogenesis has been shown to be CCR2 dependent, All D:TTNYT (SEQ ID NO: 1) has been shown to prevent and reverse neuropathic pain and microglial activation. The peptide was fed to rats in various nerve injury rat models as shown by the following sections.

CCR2 and CCR5 control trafficking of monocyte/macrophages and mediate the inflammatory response during infectious disease and tissue injury. MCP-1 is a specific ligand for CCR2, while MIP-1β is specific for CCR5. In order to identify the receptor targets of All D TTNYT (SEQ ID NO:1), we tested the ability of All D TTNYT (SEQ ID NO:1) to antagonize the function of chemokine receptors by blocking the chemotactic migration of human monocytes in the presence of specific ligand. Monocytes were treated for 30 minutes, 37° C. with All D TTNYT (SEQ ID NO:1) before testing. The results (FIG. 9) showed that All D TTNYT (SEQ ID NO:1) was a potent antagonist of both CCR2 ($IC_{50}$ 4.2 pM) and CCR5 ($IC_{50}$ 0.18 pM). All D TTNYT (SEQ ID NO:1) was apparently 20-fold more potent at blocking MIP-1β compared to MCP-1 chemotaxis. All D TTNYT (SEQ ID NO:1) also blocked chemotaxis of the astroglial cell line U87-CCR2, with similar potency (data not shown).

6. Oral Administration of all D TTNYT (SEQ ID NO:1) Potently Attenuated Nerve Injury Induced Mechanical and Thermal Hypersensitivity All D TTNYT (SEQ ID NO:1) Prevented the Development of Neuropathic Pain.

To test the hypothesis that All D TTNYT (SEQ ID NO:1) alleviates behavioral signs of neuropathic pain, we first evaluated the effects of All D TTNYT (SEQ ID NO:1) on the development of mechanical allodynia and thermal hyperalgesia in rats following nerve injury. Rats started to receive All D TTNYT (SEQ ID NO:1) or saline on the day of the surgery and the drug was delivered orally, once per day and the treatment lasted for 7 days. Shortly after partial ligation of the left sciatic nerve, rats receiving saline showed an exaggerated bilateral decrease of paw withdrawal threshold in response to von Frey hair stimulation (FIG. 10A-B) and a sharp unilateral response to heat stimuli (FIG. 10C-D) at the plantar surface, which confirmed a similar observation reported originally by Seltzer et al [27]. Oral administration of All D TTNYT (SEQ ID NO:1) for 7 days almost completely prevented the development of mechanical allodynia induced by nerve injury, e.g., oral daily All D TTNYT (SEQ ID NO:1) (1 mg/kg b.w) reached 106±33% and 88±32% attenuation of mechanical allodynia at 3 days and at 7 days post-injury, respectively. Paw withdrawal threshold in response to von Frey hair stimulation in rats treated with All D TTNYT (SEQ ID NO:1) was 11.23±2.26 g (day 3) and 9.89±2.39 g (day 7) vs. 3.84±0.45 and 2.91±0.37 g in animals receiving saline treatment (p<0.001 vs. saline treated), whereas pre-surgery paw withdrawal latency was 10.83±0.71 g (FIG. 2A). All D TTNYT (SEQ ID NO:1) given systemically also improved the mechanical sensitivity at the contralateral side (FIG. 11B). The efficacy of All D TTNYT (SEQ ID NO:1) on nerve injury-induced thermal hyperalgesia was assessed in the same group of animals at day 4 and day 6 post-injury. All three tested doses (0.05, 0.1, 1 mg/kg b.w.) resulted in a sustained attenuation of thermal hyperalgesia (FIG. 11C). The effects were less potent than that observed in mechanical sensitivity testing, ranging from 43±11% to 67±22% reduction at different time points with 1 mg/kg b.w. There was no significant difference for three doses in paw withdrawal threshold and latency with preventive paradigm. All D TTNYT (SEQ ID NO: 1) did not alter paw withdrawal threshold and latency in naïve animals (data not shown).

All D TTNYT (SEQ ID NO:1) Reversed Already Established Neuropathic Pain.

We also examined the effects of All D TTNYT (SEQ ID NO:1) on already established hypersensitivity following nerve lesion. All D TTNYT (SEQ ID NO:1) was given orally on day 8 post-injury, where both paw withdrawal threshold and latency in response to mechanical and thermal stimuli, respectively, had already reached their lowest level (FIG. 11). The treatment continued afterwards for 4 days. As revealed in FIG. 11A-B, the dose of 0.1 mg/kg b.w. of All D TTNYT (SEQ ID NO:1) was not able to reverse the mechanical allodynia at both ipsi- and contralateral sides, but partially rescued the low withdrawal latency in response to heat stimuli at day 8 (FIG. 11C). However, the dose of 0.2 mg/kg b.w. started to exhibit more consistent effect in reversing both mechanical and thermal hypersensitivity, e.g., the paw withdrawal threshold reached 5.45±1.11 g at day 9 and 6.72±1.24 g at day 11 in All D TTNYT (SEQ ID NO:1) treated rats vs 2.06±0.13 g and 2.11±0.44 g in rats treated with saline at their respective time points; the paw withdrawal latency reached 9.28±2.04 s at day 8 and 10.82±1.48 s at day 10 in All D TTNYT (SEQ ID NO:1) treated rats vs 5.23±0.32 s and 5.71±0.76 s in rats treated with saline at their respective time points (FIG. 11A, 11C). The dose of 1 mg/kg b.w. also effectively reversed the nerve injury evoked hypersensitivity (FIG. 11).

7. All D TTNYT (SEQ ID NO:1) Inhibited Nerve Injury Induced Spinal Microglial Activation In order to understand the potential underlying mechanisms in relieving pain behavior, we examined the effects of All D TTNYT (SEQ ID NO:1) on spinal microglia. In nerve-injured rats receiving saline treatment, there was a strong increase in Iba-1 immunoreactivity (ir) condensed at the ipsilateral side of spinal DH and VH at 7 days post-surgery. This pattern of microglial expression was no longer observed in rats treated with All D TTNYT (SEQ ID NO:1) (FIG. 4A). High magnification images revealed that stereotypical microglial morphology during activation were also prevented by All D TTNYT (SEQ ID NO:1). Seven days after nerve injury, without All D TTNYT (SEQ ID NO:1) treatment, microglia in the spinal cord, ipsilateral side to the injury, displayed large cell bodies, shorten and thick branches, and intense Iba-1 labeling, whereas Iba-1$^+$ cells in the spinal cord of All D TTNYT (SEQ ID NO:1)-treated rats had small cell bodies with long and fine ramifications and much less intense Iba-1 staining (FIG. 4A). To compare with naïve rats, nerve injury dramatically increased the total surface occupied by Iba-1$^+$ cells on the ipsilateral side spinal cord DH and VH, which reflects a significant increase of cell number and an enlargement of cell size, two major characteristics of microglial cell activation. The nerve injury induced spinal microglial activation was inhibited by a-7 day preventive All D TTNYT (SEQ ID NO:1) treatment and also attenuated by a reversal All D TTNYT (SEQ ID NO:1) treatment paradigm (FIG. 4B). Moreover, by blocking both CCR2 and CCR5, All D TTNYT (SEQ ID NO:1) successfully prevented the infiltration of bone marrow derived monocytes/macrophages from circulation into the spinal cord parenchyma (FIG. 4C). Fourteen days after the nerve injury, cluster of ramified GFP$^+$ cells found in the spinal parenchyma DH (14.09±2.27) and VH (27.03±2.58) was reduced to 4.22±0.98 and 7.69±1.89, respectively, with the presence of All D TTNYT (SEQ ID NO:1) (FIG. 4D).

8. The Effect of all D TTNYT (SEQ ID NO:1) on Nerve Injury Induced Spinal Astrocyte Activation As nerve injury induced microglia and astrocytes activation usually occurred together, we also examined the effects of All D TTNYT (SEQ ID NO:1) on astrocyte activation in the spinal cord following nerve injury. Spinal astrocytes were labelled with an antibody against glial fibrillary acid protein (GFAP). Changes in GFAP ir after peripheral nerve injury are depicted in FIG. 5A. The cumulative surface occupied by GFAP+ cells within defined AOI was significantly higher than that of naïve animals; however, no significant changes were observed with the All D TTNYT (SEQ ID NO:1) preventive treatment (FIG. 5B). Reversal paradigm had a slight effect in reducing nerve injury induced spinal astrocytes activation (FIG. 5B).

9. All D TTNYT (SEQ ID NO:1) Reduced the Increase of Cytokines in the Spinal Cord Following the Lesion on the Sciatic Nerve To explore whether All D TTNYT (SEQ ID NO:1), a potent dual CCR2/CCR5 antagonist, could alter local inflammatory response and thereby explain its potential effect on hypersensitivity, we measured levels of pro-inflammatory cytokines IL-1β and IL-6 transcripts in the spinal cords and in sciatic nerves with quantitative real time-PCR. As depicted in FIG. 6. IL-1β and IL-6 mRNAs were significantly upregulated at the ipsilateral spinal cord and in damaged sciatic nerve following nerve injury. The increase of these pro-inflammatory mediators within the spinal cords, as well as in the peripheral nerves was significantly reduced with the treatment of All D TTNYT (SEQ ID NO:1) (FIG. 6).

10. Nerve Injury Induced CCR5 Expression in Activated Spinal Microglia

As the expression of CCR2 in spinal microglia has been reported previously [2], whether CCR5 can be induced within the spinal cord by nerve injury is unclear, to gain insight into the site of action of All D TTNYT (SEQ ID NO:1) in this specific neuropathic pain condition, we examined the expression and the cellular localization of CCR5 in rat spinal cord. CCR5 mRNAs were not detected within the spinal cords of naïve rats by using in situ hybridization method (FIG. 12A). However, partial ligation on the sciatic nerve resulted in an up-regulation of the transcripts at both dorsal and ventral horns, ipsilateral to the nerve injury (FIG. 12B). Positive signals (silver grains) for CCR5 mRNAs were observed on some glial cells in both dorsal and ventral horns, which were heavily stained with thionine (FIG. 12C). Double labeling combining IHC for Iba-1 and ISH for CCR5 mRNA confirmed that these receptor transcripts (CCR5) expressing cells are Iba-1$^+$ activated microglia (FIG. 12D). In situ hybridization was also performed on DRGs. No significant positive signals for CCR5mRNAs were detected in DRG sensory neurons (data not shown).

11. CCR5 is Required for the Development of Neuropathic Pain and Spinal Microglial Activation Following Nerve Injury The critical role of CCR2 in the pathogenesis of neuropathic pain has been very well established [2; 31]. To further confirm that CCR5 is also necessary for the development of neuropathic pain, we made use of CCR5 knock-out mice. As depicted in FIGS. 7A-D, CCR5 gene deletion did not affect mice withdrawal threshold and latency to mechanical and heat stimuli without injury (baseline before surgery and contralateral paw). However, while wild-type mice showed a robust decrease in withdrawal threshold from 0.54±0.06 g before surgery to 0.16±0.03 g (p<0.001) at day 3 post-surgery, and maintained this hypersensitivity (around 0.1 g) to the end of the testing period (day 14), mechanical allodynia was completely abolished in CCR5KO mice. Similar responses were obtained to heat stimulation. CCR5KO mice did not develop thermal hyperalgesia following nerve injury and in wild-type mice, the withdrawal latency decreased from 11.36±1.09 s before to 6.73±0.27 s at day 14 post-injury. In addition, spinal microglial reaction to the peripheral nerve injury observed in wild type mice was significantly impaired in CCR5 KO mice (FIG. 2A), which was confirmed by an quantitative analysis based on the cumulative area occupied by Iba-1$^+$ cells within a defined AOI (FIG. 2B-C).

CONCLUSION

The CCR2 AND CCR5 antagonist, All D:TTNYT (SEQ ID NO:1), not only prevents the development of mechanical and thermal hypersensitivity following nerve injury, but also reverses established neuropathic pain.

Without exception the natural L-amino acid forms of these pentapeptides can be made as all D-amino acid forms with no loss of bioactivity, while protecting against inactivating proteolytic enzymes and bestowing useful pharmacodynamic properties, e.g. making oral activity possible. The "lock and key" model of peptide-receptor interactions has now been displaced with a "vibratory resonance" model.

The biological outcomes of All D:TTNYT (SEQ ID NO:1) in this context may be attributed to its inhibition of spinal microglial/astrocyte activation and local inflammatory responses by targeting the CCR2 receptor or the CCR5 receptor.

These observations make clear that neuroinflammation lies at the root of many diseases of unknown etiology and is initiated in one or more of three ways: 1) viral/microbial infection, 2) tissue trauma/injury or 3) environmental toxin exposure. The actual form the neuroinflammatory disease takes is a function of when? [e.g., first trimester (autism), second trimester (schizophrenia), after 65 years (Alzheimer's), etc] and "where?" [eg, optic nerve demylination in multiple sclerosis, spinal cord in Lou Gehrig' disease, substantia nigra of brain (Parkinson's disease, joints (arthritis), etc.] The inventors also believe that cancers associated with inflammation will respond to this treatment. This is the first report showing a benefit of All D TTNYT (SEQ ID NO:1) in a model of neuropathic pain. While CCR2 has a well established role in the inflammation underlying chronic pain, some evidence for the involvement of CCR5 in development of neuropathic pain after injury is suggested by studies showing that injection of MIP1α and RANTES into peripheral nerve elicited pain behaviors [13; 18]. Our results support such a view and, using genetically deficient animals, demonstrate that CCR5 is required for the development of neuropathic pain. Mice lacking CCR5 develop neither mechanical nor thermal hypersensitivity following injury on the nerve.

Our results further suggest that pharmacological blockade by All D TTNYT (SEQ ID NO:1) of either or both CCR2 and CCR5 have therapeutic potential in injury associated-neuropathic pain. All D TTNYT (SEQ ID NO:1) acts as a potent antagonist for both CCR5 and CCR2 mediated human monocyte chemotaxis. In vivo experiments revealed that this dual antagonist is orally active and exerts potent antiallodynic and antihyperalgesic effects in both preventive and reversal treatment paradigms in rats following peripheral nerve injury. All D TTNYT (SEQ ID NO:1) relieves neuropathic pain through reducing CCR2/CCR5 mediated inflammatory reaction, since in parallel with the behavioral outcomes, we observed that 1) pharmacological blockade of both CCR2/CCR5 by All D TTNYT (SEQ ID NO:1) reduced spinal microglial activation triggered by nerve injury, including the abolishment of blood born monocyte/macrophage recruitment into the spinal parenchyma; 2) All D TTNYT (SEQ ID NO:1) was able to prevent the increase of pro-inflammatory cytokines along the pain signaling pathway.

DAPTA, the parent compound from which All D TTNYT (SEQ ID NO:1) was derived, had previously been shown to have anti-inflammatory effects including inhibition of CCR5/MIP-1β chemotaxis on human monocytes [21], attenuation of neuroinflammation in an Alzheimer's disease model [25] and reduction of the inflammatory cytokines TNF-α, IL-1, and IL-6 in HIV patients [26]. In the current study, our in vitro experiments clearly demonstrated that All D TTNYT (SEQ ID NO:1) potently blocks MIP-1β and MCP-1 elicited monocyte chemotaxis with IC50s of 0.18 pM and 4.2 pM, respectively. The remarkably potent inhibitory effect of All D TTNYT (SEQ ID NO:1) on both CCR5 and CCR2 mediated monocyte trafficking suggests that dual antagonists of CCR2 and CCR5 may provide new tools for the study of chemokine signaling in different pathological conditions, and potentially therefore better treatment outcomes.

The roles of MCP-1/CCR2 signaling in chronic pain have been well documented. Over-expression of MCP-1 showed enhanced pain sensitivity [17]. Neutralizing MCP-1 prevented the development of nerve injury evoked hypersensitivity [10]. Drugs that block CCR2 receptors can reduce hypersensitivity in HIV [5] and focal nerve demyelination [4] associated peripheral neuropathy. Lack of CCR2 in mice impaired the development of mechanical allodynia following nerve injury [2; 31]. Relative to CCR2, the function of CCR5 in chronic pain is less well defined. However, some recent evidence suggested the potential involvement of CCR5 in different aspects of pain modulation. Microinjection of RANTES, a natural ligand for CCR5, into the periaqueductal grey, a brain region critical to the processing of pain signals, induced hyperalgesia, which was prevented by pretreatment with antibodies against RANTES [3]. Partial sciatic nerve ligation induced expression of MIP-1a, another natural ligand for CCR5, on macrophages and Schwann cells in injured nerve. Tactile allodynia and thermal hyperalgesia developed following nerve lesion was prevented by perineural injection of neutralising anti-MIP-1α and CCR5 siRNA [13]. The results yielded from our current investigation using CCR5 KO mice clearly demonstrated that similar to CCR2, CCR5 is required for the development of neuropathic pain following nerve injury. Pharmacological intervention with All D TTNYT (SEQ ID NO: 1), a dual antagonist of both CCR2 and CCR5, delivered orally, not only prevented the initiation of mechanical and thermal hypersensitivity, but also reversed both mechanical and thermal hypersensitivity already established in rats having ligation on the sciatic nerve.

Together with its analgesic effect, we also observed that All D TTNYT (SEQ ID NO:1) efficiently inhibited spinal microglial activation, including changes in cell number, cell size and cell shape. In addition, All D TTNYT (SEQ ID NO:1) successfully blocked the entrance of blood born monocytes/macrophages into the spinal cord parenchyma. All these most likely occurred through the interaction of All D TTNYT (SEQ ID NO:1) with both CCR2 and CCR5 receptors present on circulating monocytes, macrophages and activated spinal microglia. Both CCR2 [31] and CCR5 KO (current study) mice exhibited an impaired microglial response following an injury on the nerve. In coincidence with the inhibition of microglial activation, the levels of some pro-inflammatory cytokines, such as IL-1β and IL-6, most likely released by activated spinal glial cells and peripheral immune cells, were also reduced with the treatment of All D TTNYT (SEQ ID NO:1). The roles of these pro-inflammatory mediators in the pathophysiology of neuropathic pain has been extensively studied [23]. They contribute significantly to enhance excitability of sensory neurons and to maintain pathological pain states. Therefore, we assume that All D TTNYT (SEQ ID NO:1) attenuate mechanical and thermal hypersensitive response, at least partially, through modulation of nerve injury induced glial activation and subsequent inflammatory reaction.

Because of their key roles in inflammation related diseases, CCR2 and CCR5 constitute attractive therapeutic targets. However, it should be noted that the chemokine network is notorious for its redundancy and receptor promiscuity. Apparent redundancy in the chemokine system, such as CCR2 and CCR5, might exist to confer robustness to the control of inflammation [7; 8; 12]. Moreover, the fact that chemokine receptors form hetero-oligomeric complexes composed of at least three chemokine receptors CCR2, CCR5, and CXCR4, bring an additional layer of complexity to this system [29]. Specific antagonism of one chemokine receptor can lead to functional cross-inhibition of the others [29]. It is perhaps more correct to consider that the functional and biologically relevant therapeutic targets are the naturally occurring mixed receptor complexes. Heterologous desensitization of CCR2-mediated responses may provide an explanation for the functional action of All D TTNYT (SEQ ID NO:1), which is derived from the CCR5 antagonist DAPTA [19]. CCR5 expression is low on resting cells and its up-regulation after injury, in the context of likely hetero-dimer formation may serve to attenuate or limit further CCR2 driven inflammation. CCR2 may be more important for early migration responses into injured spinal cord, as CCR5 is low. As CCR5 becomes expressed, and R5 ligands are locally released, the CCR5 pathways also contribute to spinal microglial reactions.

The action of All D TTNYT (SEQ ID NO:1) to limit CCR2 responses causing chronic pain may or may not occur directly via CCR2, but rather as a consequence of CCR5-mediated desensitization of CCR2 [29]. This model of joint CCR2/CCR5 interaction could help explain why selective or "pure" receptor-targeted therapeutic compounds that antagonize single chemokine receptors afford little efficacy in clinical use [32]. Useful antagonists might block multiple receptors, or could target a functional receptor complex, rather than constituent single receptors. Receptor oligomerization represents a regulatory mechanism for a more nuanced control of CCR2 and CCR5 driven inflammatory activation that might be exploited clinically. Drugs that block more than one component of the chemokine system may overcome the functional redundancy and cross-regulation in the chemokine system that presumably limits effectiveness of CCR2 antagonists and might be a more efficacious strategy than targeting either receptor alone. Our results support these hypotheses since a novel and potent, orally active dual CCR2/CCR5 antagonist, All D TTNYT (SEQ ID NO:1), has multiple benefits in injury induced-neuropathic pain.

In conclusion, we provided evidence that in addition to chemokine receptor CCR2, CCR5 is equally necessary for the development of neuropathic pain. Based on the structural similarity and functional redundancy in controlling monocytes/macrophages trafficking and spinal microglial reaction, we suggest that dual targeting CCR2/CCR5 should provide greater efficacy than targeting CCR2 or CCR5 alone and All D TTNYT (SEQ ID NO:1) has the potential for broad clinical use in neuropathic pain treatment.

All D TTNYT (SEQ ID NO:1) has the ability to block monocyte chemotaxis mediated by other chemokine receptors, for example CX3CR1, the receptor for fractalkine, at similar highly potent concentrations. (data not shown). This receptor is almost as well established in mediating painful neuropathy as CCR2. The HIV envelope (gp120) has affinity for binding to many other chemokine receptors (see review by Lokesh, Agrawal) which are not well established as mediating painful neuropathy. Thus, the ability to block many chemokine receptors, which the HIV virus has evolved, can be exploited if, as this paper suggests, duel, triple, quadruple and multiple chemokine receptor blockades, can lead to more efficacious anti-neuropathic pain activities. Thus other gp120 derived modified peptide analogs would be predicted to be highly effective.

A gp120 derived peptide is a contiguous sequence of amino acids from a gp120 envelope protein found to have the proper chemokine antagonist activity. The peptide has a length between one hundred (100) amino acids and four (4) amino acids, including each and every range and each and every length between 100 and 4. Modifications include all common peptide stabilizing modifications, including, but not limited to the use of amino acid D stereo isomers.

REFERENCE LIST

[1] Abbadie C, Bhangoo S, De K Y, Malcangio M, Melik-Parsadaniantz S, White F A. Chemokines and pain mechanisms. Brain Res Rev 2009; 60:125-134.

[2] Abbadie C, Lindia J A, Cumiskey A M, Peterson L B, Mudgett J S, Bayne E K, DeMartino J A, MacIntyre D E, Forrest M J. Impaired neuropathic pain responses in mice lacking the chemokine receptor CCR2. Proc Natl Acad Sci USA 2003; 100:7947-7952.

[3] Benamar K, Geller E B, Adler M W. Elevated level of the proinflammatory chemokine, RANTES/CCL5, in the periaqueductal grey causes hyperalgesia in rats. Eur J Pharmacol 2008; 592:93-95.

[4] Bhangoo S, Ren D, Miller R J, Henry K J, Lineswala J, Hamdouchi C, Li B, Monahan P E, Chan D M, Ripsch M S, White F A. Delayed functional expression of neuronal chemokine receptors following focal nerve demyelination in the rat: a mechanism for the development of chronic sensitization of peripheral nociceptors. Mol Pain 2007; 3:38.

[5] Bhangoo S K, Ripsch M S, Buchanan D J, Miller R J, White F A. Increased chemokine signaling in a model of HIV1-associated peripheral neuropathy. Mol Pain 2009; 5:48.

[6] Chaplan S R, Bach F W, Pogrel J W, Chung J M, Yaksh T L. Quantitative assessment of tactile allodynia in the rat paw. J Neurosci Methods 1994; 53:55-63.

[7] Combadiere C, Potteaux S, Rodero M, Simon T, Pezard A, Esposito B, Merval R, Proudfoot A, Tedgui A, Mallat Z. Combined inhibition of CCL2, CX3CR1, and CCR5 abrogates Ly6C(hi) and Ly6C(lo) monocytosis and almost abolishes atherosclerosis in hypercholesterolemic mice. Circulation 2008; 117:1649-1657.

[8] Dean M, Carrington M, Winkler C, Huttley G A, Smith M W, Allikmets R, Goedert J J, Buchbinder S P, Vitting-hoff E, Gomperts E, Donfield S, Vlahov D, Kaslow R, Saah A, Rinaldo C, Detels R, O'Brien S J. Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science 1996; 273:1856-1862.

[9] Dixon W J. Efficient analysis of experimental observations. Annu Rev Pharmacol Toxicol 1980; 20:441-462.

[10] Gao Y J, Zhang L, Samad O A, Suter M R, Yasuhiko K, Xu Z Z, Park J Y, Lind A L, Ma Q, Ji R R. JNK-induced MCP-1 production in spinal cord astrocytes contributes to central sensitization and neuropathic pain. J Neurosci 2009; 29:4096-4108.

[11] Hargreaves K, Dubner R, Brown F, Flores C, Joris J. A new and sensitive method for measuring thermal nociception in cutaneous hyperalgesia. Pain 1988; 32:77-88.

[12] Karlmark K R, Wasmuth H E, Trautwein C, Tacke F. Chemokine-directed immune cell infiltration in acute and chronic liver disease. Expert Rev Gastroenterol Hepatol 2008; 2:233-242.

[13] Kiguchi N, Maeda T, Kobayashi Y, Fukazawa Y, Kishioka S. Macrophage inflammatory protein-1alpha mediates the development of neuropathic pain following peripheral nerve injury through interleukin-1beta up-regulation. Pain 2010.

[14] Livak K J, Schmittgen T D. Analysis of relative gene expression data using real-time quantitative PCR and the 2(-Delta Delta C(T)) Method. Methods 2001; 25:402-408.

[15] Malmberg A B, Basbaum A I. Partial sciatic nerve injury in the mouse as a model of neuropathic pain: behavioral and neuroanatomical correlates. Pain 1998; 76:215-222.

[16] Mellado M, Vila-Coro A J, Martinez C, Rodriguez-Frade J M. Receptor dimerization: a key step in chemokine signaling. Cell Mol Biol (Noisy-le-grand) 2001; 47:575-582.

[17] Menetski J, Mistry S, Lu M, Mudgett J S, Ransohoff R M, DeMartino J A, MacIntyre D E, Abbadie C. Mice overexpressing chemokine ligand 2 (CCL2) in astrocytes display enhanced nociceptive responses. Neuroscience 2007; 149:706-714.

[18] Oh S B, Tran P B, Gillard S E, Hurley R W, Hammond D L, Miller R J. Chemokines and glycoprotein120 produce pain hypersensitivity by directly exciting primary nociceptive neurons. J Neurosci 2001; 21:5027-5035.

[19] Polianova M T, Ruscetti F W, Pert C B, Ruff M R. Chemokine receptor-5 (CCR5) is a receptor for the HIV entry inhibitor peptide T (DAPTA). Antiviral Res 2005; 67:83-92.

[20] Raport C J, Gosling J, Schweickart V L, Gray P W, Charo I F. Molecular cloning and functional characterization of a novel human C C chemokine receptor (CCR5) for RANTES, MIP-1beta, and MIP-1alpha. J Biol Chem 1996; 271:17161-17166.

[21] Redwine L S, Pert C B, Rone J D, Nixon R, Vance M, Sandler B, Lumpkin M D, Dieter D J, Ruff M R. Peptide T blocks GP120/CCR5 chemokine receptor-mediated chemotaxis. Clin Immunol 1999; 93:124-131.

[22] Ren K, Dubner R. Interactions between the immune and nervous systems in pain. Nat Med 2010; 16:1267-1276.

[23] Ren K, Torres R. Role of interleukin-1beta during pain and inflammation. Brain Res Rev 2009; 60:57-64.

[24] Ribeiro S, Horuk R. The clinical potential of chemokine receptor antagonists. Pharmacol Ther 2005; 107:44-58.

[25] Rosi S, Pert C B, Ruff M R, Gann-Gramling K, Wenk G L. Chemokine receptor 5 antagonist D-Ala-peptide T-amide reduces microglia and astrocyte activation within the hippocampus in a neuroinflammatory rat model of Alzheimer's disease. Neuroscience 2005; 134:671-676.

[26] Ruff M R, Polianova M, Yang Q E, Leoung G S, Ruscetti F W, Pert C B. Update on D-ala-peptide T-amide (DAPTA): a viral entry inhibitor that blocks CCR5 chemokine receptors. Curr HIV Res 2003; 1:51-67.

[27] Seltzer Z, Dubner R, Shir Y. A novel behavioral model of neuropathic pain disorders produced in rats by partial sciatic nerve injury. Pain 1990; 43:205-218.

[28] Serrano A, Pare M, McIntosh F, Elmes S J, Martino G, Jomphe C, Lessard E, Lembo P M, Vaillancourt F, Perkins M N, Cao C Q. Blocking spinal CCR2 with AZ889 reversed hyperalgesia in a model of neuropathic pain. Mol Pain 2010; 6:90.

[29] Sohy D, Yano H, de N P, Urizar E, Guillabert A, Javitch J A, Parmentier M, Springael J Y. Hetero-oligomerization of CCR2, CCR5, and CXCR4 and the protean effects of "selective" antagonists. J Biol Chem 2009; 284:31270-31279.

[30] Zhang J, Rivest S. Distribution, regulation and colocalization of the genes encoding the EP2- and EP4-PGE2 receptors in the rat brain and neuronal responses to systemic inflammation. Eur J Neurosci 1999; 11:2651-2668.

[31] Zhang J, Shi X Q, Echeverry S, Mogil J S, De Koninck Y, Rivest S. Expression of CCR2 in both resident and bone marrow-derived microglia plays a critical role in neuropathic pain. J Neurosci 2007; 27:12396-12406.

[32] Zhao Q. Dual targeting of CCR2 and CCR5: therapeutic potential for immunologic and cardiovascular diseases. J Leukoc Biol 2010.

What is claimed is:

1. A method of treatment of pain from inflammation comprising
    preparing an all D TTNYT (SEQ ID NO:1) pharmaceutical composition comprising,
        an all D TTNYT (SEQ ID NO:1) peptide,
        a pharmaceutically effective carrier, and
    administering said pharmaceutical composition in an effective dose to a patient suffering pain from inflammation.

2. The method of treatment as defined in claim 1 wherein said pain from inflammation is caused by painful neuropathy.

3. The method of treatment as defined in claim 1 wherein said pain from inflammation is caused by diabetic painful neuropathy.

4. The method of treatment as defined in claim 1 wherein said pain from inflammation is caused by a condition selected from the group consisting of:
    fibromyalgia, endometriosis, abdominal pain, arthritis, cancer, muscle pain and joint pain.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Human immunodeficiency virus

<400> SEQUENCE: 1

Thr Thr Asn Tyr Thr
1               5